United States Patent
More et al.

(10) Patent No.: US 10,578,532 B2
(45) Date of Patent: *Mar. 3, 2020

(54) AUTOMATED PROFILING OF THE HARDNESS OF WOOD

(71) Applicant: OSMOSE UTILITIES SERVICES, INC., Peachtree City, GA (US)

(72) Inventors: Randal K. More, Lafayette, NY (US); Nelson G. Bingel, III, Senoia, GA (US); Thomas Pope, Newnan, GA (US); Lawrence J. Geitner, Hamburg, NY (US)

(73) Assignee: OSMOSE UTILITIES SERVICES, INC., Tyrone, GA (US)

(*) Notice: Subject to any disclaimer, the term of this patent is extended or adjusted under 35 U.S.C. 154(b) by 107 days.

This patent is subject to a terminal disclaimer.

(21) Appl. No.: 15/872,384

(22) Filed: Jan. 16, 2018

(65) Prior Publication Data

US 2018/0136101 A1    May 17, 2018

Related U.S. Application Data

(63) Continuation of application No. 14/625,303, filed on Feb. 18, 2015, now Pat. No. 9,869,622.
(Continued)

(51) Int. Cl.
*G01N 3/42* (2006.01)
*G01N 33/46* (2006.01)
*G01N 3/40* (2006.01)

(52) U.S. Cl.
CPC .............. *G01N 3/42* (2013.01); *G01N 3/40* (2013.01); *G01N 33/46* (2013.01); *G01N 2203/0041* (2013.01); *G01N 2203/0082* (2013.01)

(58) Field of Classification Search
CPC ............ G01N 3/42; G01N 33/46; G01N 3/40; G01N 2203/0082; G01N 2203/0041
See application file for complete search history.

(56) References Cited

U.S. PATENT DOCUMENTS 1,903,524 A * 4/1933 Webster .................. G01N 3/42
 73/81
2,816,439 A * 12/1957 Hayes .................... G01N 33/02
 73/81
(Continued)

FOREIGN PATENT DOCUMENTS

FR    2760842 A1    9/1998

OTHER PUBLICATIONS

International Search Report and Written Opinion for related International Patent Application No. PCT/US2015/016370, dated Sep. 1, 2015.

*Primary Examiner* — Robert R Raevis
(74) *Attorney, Agent, or Firm* — Troutman Sanders LLP

(57) ABSTRACT

The present invention pertains to a device, system, and method for evaluating the condition of a wooden structure by automated profiling of the hardness of the structure. More particularly, the present invention is directed towards a probing device comprising a blade coupled to a resistance mechanism and a mechanical sensor for measuring the hardness of wood in a structure; a system comprising such a device, and a computing device coupled to the device that outputs the hardness measurements of the device; and a method for operating such a device and determining the condition of wood by identifying changes in hardness in a wooden structure.

20 Claims, 25 Drawing Sheets

Related U.S. Application Data

(60) Provisional application No. 61/941,882, filed on Feb. 19, 2014.

(56) References Cited

U.S. PATENT DOCUMENTS

| | | | |
|---|---|---|---|
| 2,835,127 A | 5/1958 | Scott | |
| 2,865,198 A | 12/1958 | Tschirf et al. | |
| 3,805,599 A | 4/1974 | Illman et al. | |
| 3,965,727 A * | 6/1976 | Argabrite | G01N 3/42 73/81 |
| 4,182,163 A | 1/1980 | Hoffmeyer | |
| 4,249,414 A | 2/1981 | Barth | |
| 4,343,179 A | 8/1982 | Astrom et al. | |
| 6,134,954 A | 10/2000 | Suresh et al. | |
| 6,289,734 B1 | 9/2001 | Daugela | |
| 9,869,622 B2 * | 1/2018 | More | G01N 3/42 |
| 2005/0005699 A1 | 1/2005 | Huang | |
| 2007/0046289 A1 | 3/2007 | Troxler | |
| 2010/0198530 A1 * | 8/2010 | Han | G01N 3/42 702/43 |

\* cited by examiner

AUTOMATED PROFILING OF THE HARDNESS OF WOOD

CROSS REFERENCE TO RELATED APPLICATIONS

This application is a continuation of U.S. patent application Ser. No. 14/625,303, filed Feb. 18, 2015, now U.S. Pat. No. 9,869,622, which claims priority to U.S. Provisional Application No. 61/941,882, filed Feb. 19, 2014, the entire contents and substance of which are hereby incorporated by reference in their entirety.

TECHNICAL FIELD

The present invention pertains to a device, system, and method for evaluating the condition of a wooden structure by automated profiling of the hardness of the structure. More particularly, embodiments of the present invention are directed towards a probing device comprising a blade coupled to a resistance mechanism and a mechanical sensor for measuring the hardness of wood in a structure; a system comprising such a device, and a computing device coupled to the device that outputs the hardness measurements of the device; and a method for operating such a device and determining the condition of wood by identifying changes in hardness in a wooden structure.

BACKGROUND OF THE INVENTION

The regular inspection of wooden structures such as utility poles, support pilings, and other timber structures is an essential part of the maintenance and upkeep of such structures. Aging wood can suffer from internal decay and/or rot as a result of insect and fungal infestations, as well as the presence of excessive moisture in the wood, and can develop voids, cracks, and cavities in its structure. Such flaws in the structural integrity of a utility pole or other wooden structure can lead to a loss of strength in the structure, decreasing the load that can be borne by the structure and in some cases necessitating restoration or even replacement. Therefore, accurate and repeatable methods of assessing the condition of wooden structures are required to minimize the risks associated with the aging of these structures.

The keys to utility pole inspection are identifying decay, measuring defects and estimating the percent remaining strength to determine whether the utility pole passes or fails the inspection, or requires remedial attention, such as supplemental wood preservative treatment, or reinforcement or restoration. Attempts to develop pole inspection instruments have not yet fully succeeded to add value or lower costs, and there is a need in the art for alternatives to the methods and devices that currently exist for the evaluation of utility poles.

Wood is a highly variable material and there are many possible decay patterns that are possible in any particular utility pole. These decay patterns also differ by the species of wood. The most accurate option for pole inspection remains a highly trained, professional inspector using time-proven procedures and tools. Some of these procedures include the following:

Visual inspection, or visual inspection combined with sound inspection procedures are typically suitable for identifying gross defects in utility poles that may be visible above the ground level. Using the visual inspection technique, trained personnel inspect the exterior of a utility pole or other wooden structure looking for structural deficiencies such as visible cracks, fissures, and splits in the surface of the structure, plant life or algae growing on the wood, and holes bored by woodpeckers or insects. Visual inspection, alone, can be suitable for identifying gross defects visible in a wooden structure, but can produce variable results that depend on the experience and the diligence of the particular inspector.

Sound and bore procedures allow an inspector to bore inspection holes after hammer sounding identifies areas where decay may exist in a utility pole. A shell thickness indicator may also be used to measure internal decay. For example, "sound and prod" and "sound and bore" techniques involve inspection personnel "sounding" the structure by striking it with a hammer, spike, or other instrument and listening to the resulting sound for hollow-sounding noises or other audible indications of internal deficiencies. The inspection personnel next may engage in "prodding" or "probing" the pole by inserting a screwdriver, drill, or other boring tool to sample the interior of the pole or other structure in a search for decay or damage. Personnel may also scrape the exterior of the wood to look for surface decay.

Partial excavation plus sound and bore procedures allow an inspector to access a portion of the pole below ground. These procedures are useful for the identification of external decay and termites. Excavation to a depth of 18 inches to 24 inches plus sound and bore techniques allow the most complete access to the decay-prone region of poles, where moisture and oxygen encourage decay.

Electronic inspection devices are instruments that typically depend on theories, such as frequency or time of flight of a sonic wave, or physical characteristics such as hardness of wood to identify anomalies in a utility pole. For example, the Shigometer can identify early stages of decay, but it is not a pass/fail device. Other non-invasive or minimally-invasive inspection methods use equipment such as the Resistograph®, which measures the energy required to maintain a constant drilling speed in a wooden structure, or the Pilodyn penetrometer, which measures the depth into which a pre-loaded spring forces a pin into the surface of a wooden structure.

There remains a need in the art for alternative minimally-invasive techniques to complement existing techniques for the inspection of utility poles and other wooden structures, particularly for the detection of incipient decay and external decay below ground without excavation. The devices, systems, and methods of the present invention are designed to meet this and other needs.

SUMMARY OF THE INVENTION

Embodiments of the present invention are directed to a probing device for measuring the hardness of a wooden structure comprising a shaft, a distance sensor, a blade, a resistance mechanism, and a mechanical sensor.

In certain embodiments, the distance sensor of the probing device is mounted to the shaft and measures a location of the blade in a wooden structure. In further embodiments, the distance sensor is mounted to the shaft such that the distance sensor is oriented with respect to the shaft at an angle between about 0 degrees and about 60 degrees. In certain embodiments, the angle between the distance sensor and the shaft is adjustable. In certain preferred embodiments, the distance sensor comprises short-range sonar or a potentiometer.

In certain embodiments, the blade of the probing device is attached to the shaft, and coupled to the resistance mechanism, such that the blade protrudes from the shaft at a non-zero angle. In certain embodiments the blade protrudes from the shaft at an angle of about 90 degrees, such that the blade is substantially perpendicular to the shaft. In certain embodiments, the blade penetrates a wooden structure at locations within the structure where the hardness of the wood is irregular, compared to a reference wood. In other embodiments, the blade does not penetrate a wooden structure at locations within the structure where the hardness of the wood is normal, compared to a reference wood. In certain embodiments, the blade is substantially triangular in shape. In certain embodiments, the probing device comprises more than one blade.

In certain embodiments, the resistance mechanism permits the blade to retract into the shaft, according to an applied force on the blade. In certain embodiments, the resistance mechanism comprises a spring or a tensioned wire. In certain embodiments, the amount of resistance provided by the resistance mechanism to the blade may be adjusted by a user.

In certain embodiments, the mechanical sensor is coupled to the blade and measures an amount that the blade penetrates a wooden structure at a location within the structure. In certain embodiments, the mechanical sensor is a load cell or a displacement transducer.

In certain embodiments the shaft is substantially rigid. In further embodiments, the shaft is electrically non-conductive.

In certain embodiments, the shaft has a first end and a second end, wherein the distance sensor is mounted to the first end of the shaft, and the blade is attached to the second end of the shaft, wherein the distance sensor measures a location of the blade within a wooden structure.

In certain embodiments, the resistance mechanism is mechanically coupled to the blade such that the blade protrudes from the shaft at a non-zero angle, wherein the resistance mechanism permits the blade to retract into the shaft according to a predetermined applied force on the blade. In certain embodiments, the amount that the blade retracts into the shaft when inserted into the structure (or alternatively, the amount that the blade penetrates the structure), indicates the change in hardness of the wood surrounding the blade.

In certain embodiments, the mechanical sensor is coupled to the blade, wherein the mechanical sensor measures an amount that the blade penetrates a wooden structure at a location within the structure.

The present invention is directed, in certain embodiments, to a system for evaluating the hardness of a wooden structure comprising: a probing device, the probing device including a shaft, a distance sensor, and a blade coupled to a resistance mechanism and a mechanical sensor; and a machine for receiving and processing data from the probing device, wherein the machine is linked to the probing device. In certain embodiments, the machine receives from the probing device an amount that the blade of the probing device penetrates the wood at a location within the structure.

In certain embodiments of the invention, the machine is mounted on the probing device. In certain embodiments, the machine is physically remote from the probing device. In certain embodiments, the machine includes a display screen indicating the penetration resistance and/or hardness of the wood surrounding the blade, among other data. In certain embodiments, the machine includes a printer that provides such data.

In certain embodiments, the system further comprises a boring operation to create a hole in the wooden structure for introduction of the probing device.

In certain embodiments, the machine receives a plurality of amounts the blade penetrates the structure at a plurality of locations within the structure, each amount corresponding to one location, to create a hardness profile of the structure. In certain embodiments, the machine compares the hardness profile of the structure to a reference hardness profile to determine the condition of the structure.

The present invention is directed, in certain embodiments, to methods of assessing a wooden structure using a probing device, the probing device including a shaft, a distance sensor, and a blade coupled to a resistance mechanism and a mechanical sensor. In certain embodiments, the methods comprise introducing a hole into a wooden structure, or using an existing hole, and introducing the probing device.

The present invention is directed, in certain embodiments, to methods for evaluating the hardness of a wooden structure, comprising inserting a blade into the structure, the blade being coupled to a resistance mechanism; determining a location of the blade within the wooden structure with a distance sensor; measuring an amount the blade penetrates the structure at a given location using a mechanical sensor coupled to the blade and the resistance mechanism; and moving the blade deeper in the wooden structure while continuing to determine the location of the blade within the structure and measuring the amount the blade penetrates the structure.

By way of example, when a wooden structure is first placed into service, the condition of the wood therein is expected to be essentially homogenous. As used herein, "condition" refers to the state of a structure relative to "reference wood." The term "reference wood" refers to wood that is substantially undegraded. Different states of a structure relative to reference wood include but are not limited to intact, dried wood, such as the type of wood present in a wooden structure when said structure is first placed into service, wood with elevated moisture content, which is one indication of pre-decay, decayed wood, damaged wood (including but not limited to mechanical damage), and the like. Changes in the hardness of wood within a wooden structure are indicative of a change in the condition of the wood within the structure. When the hardness of the wood surrounding the mechanical sensor is essentially the same as the hardness of the reference wood, the condition of the evaluated wood is considered "normal." As used herein, "normal" or "normal wood" refers to wood that displays essentially the same hardness profile as a reference wood. "Normal wood" has the same condition as "reference wood." When the hardness of the wood surrounding the blade is different (not essentially the same) than "reference wood," the condition of the evaluated wood is considered "decayed," "damaged" or "altered."

In certain embodiments, the blade, the resistance mechanism, the distance sensor, and the mechanical sensor are components of a single device. In certain embodiments, the resistance mechanism permits the blade to retract according to an applied force on the blade.

In certain embodiments, the step of inserting the blade into the structure comprises inserting the blade into a hole in the structure. In certain embodiments, the hole in the structure is bored by an operator.

In certain embodiments, the amount the blade penetrates the wooden structure indicates the hardness of the wood surrounding the blade at a location within the structure. In certain embodiments, the hardness of the structure indicates the condition of the wood at a location within the structure.

In certain embodiments, the step of moving the blade deeper into the structure comprises moving the blade completely through the structure, to measure the hardness of one or more outer layers, or shell layers, of the structure.

In certain embodiments, the methods further comprising recording a plurality of amounts the blade penetrates the wooden structure at a plurality of locations within the structure, each amount corresponding to one location, to create a hardness profile of the structure; and, in certain embodiments, further comprising comparing a hardness profile of the structure to a reference hardness profile to determine the condition of the structure.

The present invention also provides methods for determining the capacity remaining in a structure or determining whether a structure is suitable for a particular load. In one aspect of the invention, said methods comprise the steps of determining the hardness of wood at a plurality of locations within the wooden structure; determining the location of each determined hardness within the wooden structure; comparing the hardness at a plurality of locations within the wooden structure to a hardness of a reference wood to prepare a profile of the condition of the wooden structure; and utilizing the profile of the condition of the wooden structure to estimate the remaining strength of the wooden structure.

The present invention also provides methods for identifying structures for remedial preservative treatment comprising the steps of determining the hardness of wood at a plurality of locations within the wooden structure; determining the location of each determined hardness within the wooden structure; comparing the hardness at a plurality of locations within the wooden structure to a hardness of a reference wood to prepare a profile of the condition of the wooden structure; and utilizing the profile of the condition of the wooden structure to determine whether the wooden structure should be rehabilitated.

The present invention also provides methods for the regular inspection and maintenance of in-place wooden structures comprising the steps of selecting a wooden structure as a representative wooden structure; determining the hardness of wood at a plurality of locations within the wooden structure; determining the location of each determined hardness within the wooden structure; and comparing the hardness at a plurality of locations within the wooden structure to a hardness of a reference wood to prepare a profile of the condition of the wooden structure.

The present invention also provides methods for the planning of future inspection and maintenance actions of in-place wooden structures comprising the steps of determining the hardness of wood at a plurality of locations within the wooden structure; determining the location of each determined hardness within the wooden structure; comparing the hardness at a plurality of locations within the wooden structure to a hardness of a reference wood to prepare a profile of the condition of the wooden structure; and determining whether to accelerate or decelerate a schedule for future inspection and maintenance actions for the wooden structure based on the profile of the condition of the wooden structure.

The present invention also provides methods for identifying a serviceable in-place wooden structure comprising the steps of determining the hardness of wood at a plurality of locations within the wooden structure; determining the location of each determined hardness within the wooden structure; comparing the hardness at a plurality of locations within the wooden structure to a hardness of a reference wood to prepare a profile of the condition of the wooden structure; and applying at least one remedial treatment selected from the group consisting of an external preservative, a liquid internal preservative, a solid internal preservative, and a fumigant, to the wooden structure.

The present invention also provides methods for identifying a reinforceable in-place wooden structure that has been rejected due to no longer meeting code strength requirements comprising the steps of determining the hardness of wood at a plurality of locations within the wooden structure; determining the location of each determined hardness within the wooden structure; comparing the hardness at a plurality of locations within the wooden structure to a hardness of a reference wood to prepare a profile of the condition of the wooden structure; and reinforcing the wooden structure by splinting or stubbing the wooden structure with at least one of steel channel, fiberglass, and epoxy.

The present invention also provides methods for identifying a remedial preservative treatment, reinforcement or replacement candidate in-place wooden structure comprising the steps of determining the hardness of wood at a plurality of locations within the wooden structure; determining the location of each determined hardness within the wooden structure; comparing the hardness at a plurality of locations within the wooden structure to a hardness of a reference wood to prepare a profile of the condition of the wooden structure; and reinforcing and/or treating the wooden structure with a preservative paste or bandage, fumigant, liquid treatment, or solid rod, or replacing the wooden structure with a structure having a sufficient level of strength.

BRIEF DESCRIPTION OF THE DRAWINGS

Appended FIGS. 1-25 depict certain non-limiting embodiments of the probing device, the system for evaluating wooden structures comprising the probing device, and the methods of evaluating and maintaining wooden structures using the probing device and/or system. The figures are not intended to limit the scope of the invention, but, instead, are intended to provide depictions of specific embodiments, features, and non-limiting characteristics of the devices, systems, and methods described herein.

FIG. 1 depicts a side view of an exemplary device of an embodiment of the present invention.

FIG. 2 depicts an end of an exemplary device of an embodiment of the present invention, wherein the shaft comprises a probing tip that surrounds the blade.

FIG. 3 depicts an end of an exemplary device of an embodiment of the present invention, wherein a distance sensor and a handle are attached to the shaft.

FIG. 4 depicts an exemplary device of an embodiment of the present invention, with the shaft removed from the distance sensor and handle.

FIG. 5 depicts the manner in which a removable shaft may be connected to the handle and distance sensor.

FIG. 6 depicts the probing tip removed from the shaft.

FIG. 7 depicts a side view of an exemplary device of an embodiment of the present invention.

FIG. 8 depicts an angled view of an exemplary device of an embodiment of the present invention having two blades.

FIG. 9 depicts a short-range sonar at a non-zero angle to the shaft of an exemplary device of an embodiment of the present invention.

FIG. 11 depicts a spring-loaded blade refracted into a shaft of an exemplary device of an embodiment of the present invention.

FIG. 12 depicts a displacement transducer connected to a spring-loaded blade on a shaft of an exemplary device of an embodiment of the present invention.

FIG. 14 depicts results from an evaluation of the hardness of an inspection hole in a utility pole.

FIG. 15 depicts a flow chart outlining steps of exemplary methods of embodiments of the present invention to assess and maintain a utility pole.

FIG. 16 depicts an end of an exemplary device of an embodiment of the present invention, wherein the shaft comprises a tube, a probing tip that surrounds the blade, and pins securing the device together.

FIG. 17 depicts an internal assembly of the end of the exemplary device shown in FIG. 16, wherein the tube portion of the shaft is removed.

FIG. 18 depicts a blade attached to a pivot arm that connects the blade to a spring and a shaft of an exemplary device of the present invention.

FIG. 19 depicts a spring of an exemplary device of the present invention.

FIG. 20 depicts an end of an exemplary device of an embodiment of the present invention, wherein a distance sensor, a handle, and a dial are attached to the shaft.

FIG. 21 depicts an electronics unit of an exemplary device of the present invention.

FIG. 22 depicts a side view of an exemplary device of an embodiment of the present invention, wherein the distance sensor is a string potentiometer, and the shaft is angled downward.

FIG. 23 depicts an overhead view of an exemplary device of an embodiment of the present invention.

FIG. 24 depicts an overhead view of a distance sensor, using collapsible scissors and potentiometer, of an embodiment of the present invention.

FIG. 25 depicts a side view of a distance sensor, using a compression sleeve and string potentiometer, of an embodiment of the present invention.

DETAILED DESCRIPTION OF THE INVENTION

Figure 1:
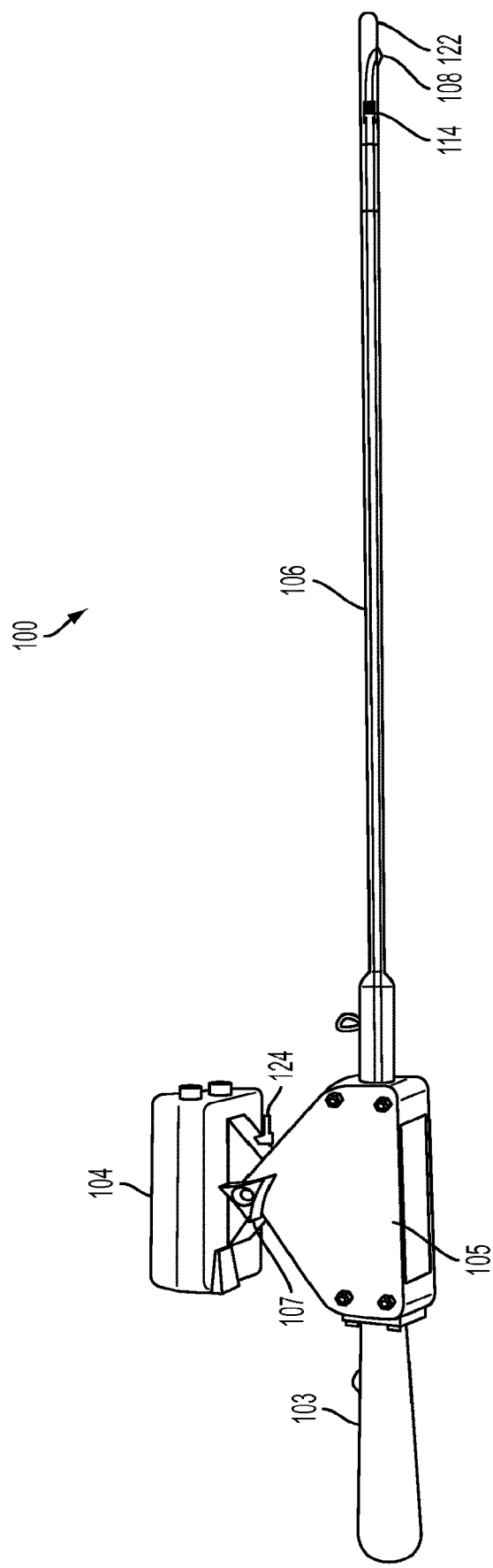

FIG. 1 depicts a side view of an exemplary probing device 100 of an embodiment of the present invention. The probing device 100 includes a horizontal handle 103, an electronics unit 105, a wireless transmitter 124, a distance sensor 104, a shaft 106, a mechanical sensor 114, a blade 108, and a probing tip 122. Although the handle is depicted in FIG. 1 as being horizontal, other orientations are envisioned as being within the scope of the invention. For example, the handle could be oriented at a non-zero angle with respect to the shaft. On the first end, a substantially rigid cylindrical shaft 106 is connected to the electronics unit 105, which includes a wireless transmitter 124 that enables data acquired by the probing device to be transmitted to a remote computing device wirelessly. In certain embodiments, the wireless transmitter 124 has Bluetooth capability. The horizontal handle 103 is attached to the electronics unit 105, and the shaft 106, such that the horizontal handle 103 is parallel to the shaft, so that an operator can insert the probing device 100 into a hole in a wooden structure. The distance sensor 104 may be a short-range sonar instrument, which emits sonar signals parallel to the shaft 106 that ping off of a wooden structure back to the distance sensor to provide the distance between the distance sensor 104 and a structure being inspected. As shown in FIG. 1, the angle of the distance sensor 104 may be adjusted by loosening a dial 107 on the side of the distance sensor 104, shifting the sensor up, and then tightening the dial to secure the distance sensor 104 at the adjusted angle. The distance sensor 104 calculates a location of the blade 108 within a structure based on the distance to the structure, the angle between the distance sensor 104 and the shaft 106, and the length of the shaft 106 up to the blade 108.

On the second end of the shaft 106, a steel blade is secured to the shaft 106 such that the sharp side of the blade 108 protrudes substantially perpendicular from the shaft 106. The shaft 106 further includes a probing tip 122 on the second end, which may, for example, slide over the blade 108, while continuing to permit the blade 108 to protrude from the shaft 106, or connect to the shaft 106 adjacent the blade 108. The probing tip 122 and the substantial remainder of the shaft 106 can be made of metal, carbon fiber, plastic, fiberglass, other composite material, or combinations thereof. The probing tip 122 can be used to guide, align, or center the shaft within a hole bored in a wooden structure. The probing tip 122 can also be used to clean out debris in a bored hole. When the probing tip 122 end of the device is inserted into a hole of a wooden structure having a slightly larger diameter than the probing tip, a resistance mechanism coupled to the blade 108 permits the blade 108 to be pushed back into the shaft 106 if the wood is of sufficient hardness to counteract the force of the resistance mechanism. The blade 108 is connected to a mechanical sensor 114 incorporated into the shaft 106. In this embodiment the mechanical sensor 114 is a strain gauge that measures the amount of strain on the resistance mechanism, which correlates to a resistance to penetration and the hardness of the wood contacting the blade 108. The strain gauge is electrically connected to the electronics unit 105, including the wireless transmitter 124, which can transmit the acquired strain data and the location data to a computing device for further processing. Alternatively, or in addition to transmitting the data, the strain data and location data can be automatically displayed on a visual display attached to the probing device 100, for example on the side of the electronics unit 105 or on top of the distance sensor 104. In certain embodiments, the visual display is an LCD indicator, which may also be used to show operating instructions.

Figure 2:
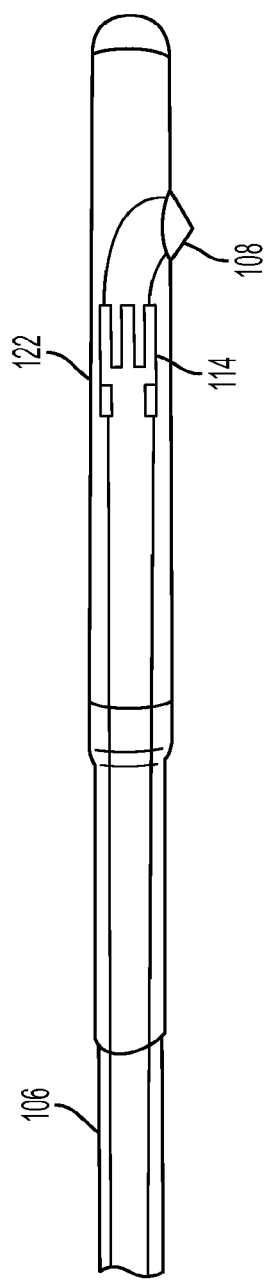

FIG. 2 depicts a close-up of the second end of an exemplary device of an embodiment of the present invention, where the shaft 106 comprises a probing tip 122 that surrounds the blade 108. The probing tip 122 is slightly larger in diameter than the substantial length of the shaft 106. For example, the probing tip 122 has a diameter of about 0.35 inches and the main portion of the shaft 106 has a diameter of about 0.30 inches. The probing tip 122 fits over the blade 108 and is secured to the remainder of the shaft 106 by a fitted adhesive sleeve, though any securing mechanism may be used. The probing tip 122 may be conically shaped for self-alignment within inspection hole 160 (not depicted). The mechanical sensor 114 is wired to the blade 108 and relays the amount the blade 108 penetrates wood at each location, quantified in this embodiment by a resistance to penetration, to the electronics unit 105 at the base of the shaft 106.

Figure 3:
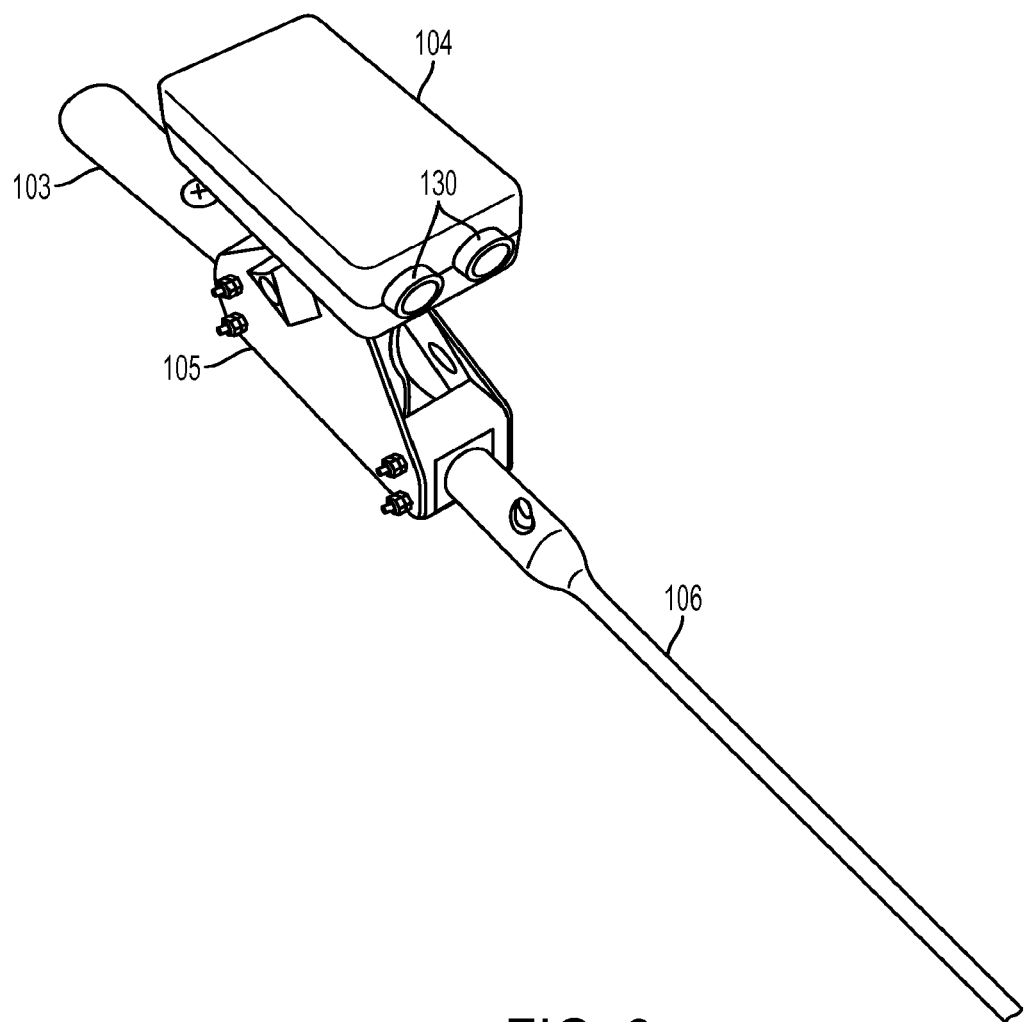

FIG. 3 depicts a close-up of the first end of an exemplary device of an embodiment of the present invention, wherein a distance sensor 104, a horizontal handle 103, and an electronics unit 105 are attached to the shaft 106. The distance sensor 104 has two sound transmitters/receivers 130 facing in the direction of the shaft 106. The distance sensor 104 has a power button to activate the device and may be battery-operated.

Figure 4:
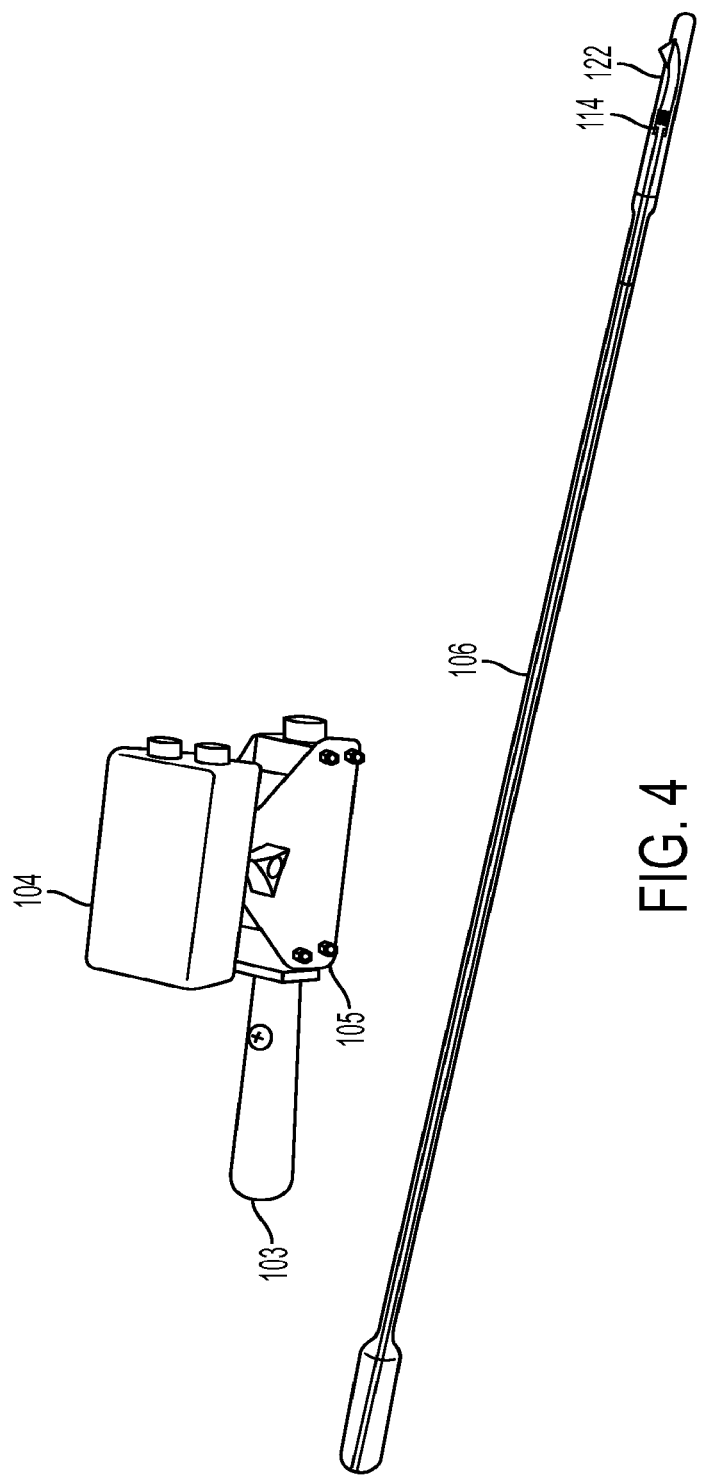

FIG. 4 depicts an exemplary device of an embodiment, with the shaft 106 removed from the electronics unit 105, distance sensor 104, and horizontal handle 103. The shaft 106 can be removed to facilitate transport of the probing device 100, or to switch out shafts of different lengths or diameters, depending on the intended inspection hole and structure. In this example, the base of the shaft 106 has a larger diameter than the rest of the shaft 106, including the probing tip 122, to support the mechanical connection between the shaft 106 and the electronics unit 105.

Figure 5:
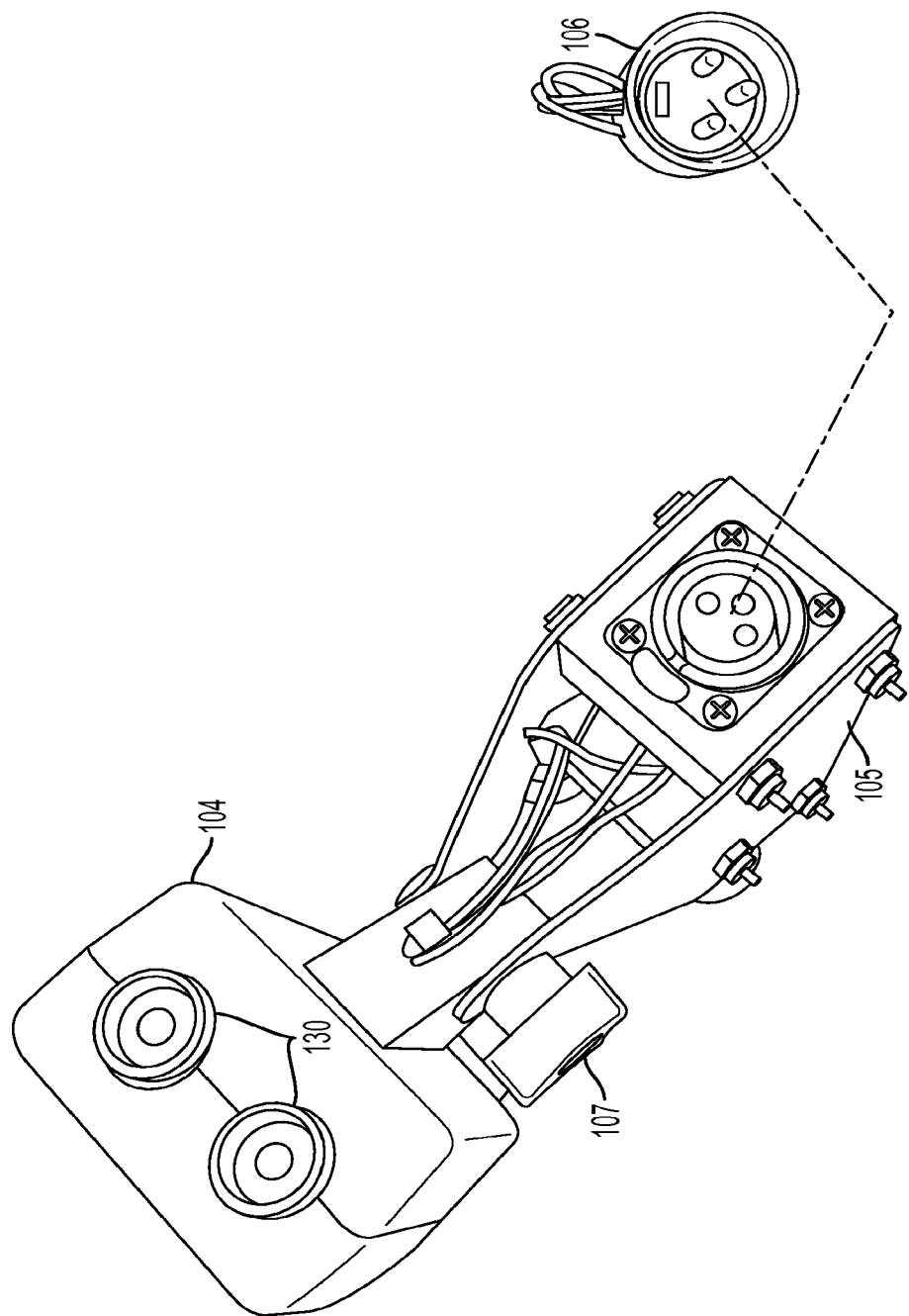

FIG. 5 depicts a connections between the removable shaft and the electronics unit 105. The enlarged base of the shaft 106 is fitted to snap into the electronics unit 105, and the three metal prongs provide the electrical connections between the components in the shaft 106 (e.g., the mechanical sensor) and the electronics unit 105. The two transmitters/receivers 130 of the distance sensor 104 are shown, as is the dial 107 permitting adjustment of the angle of the distance sensor 104.

Figure 6:
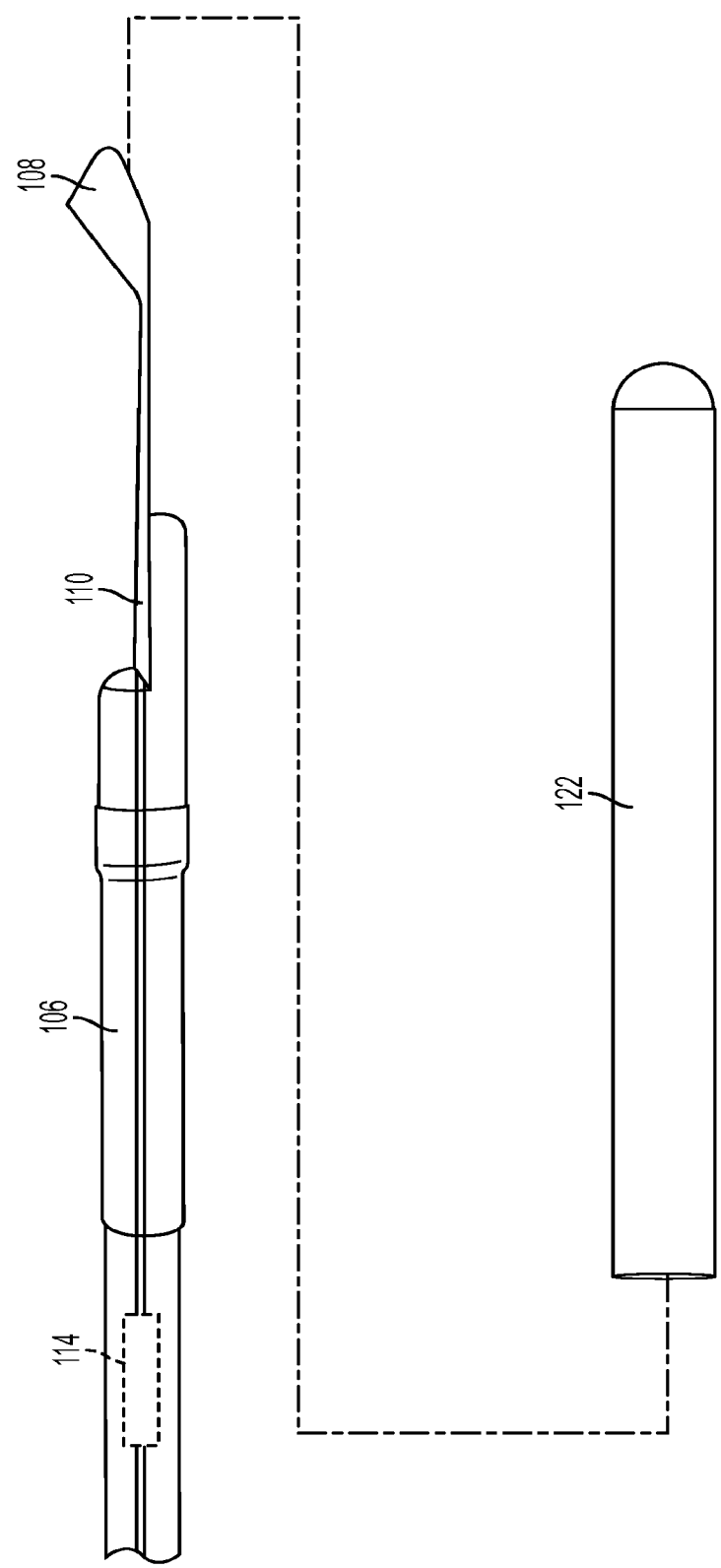

FIG. 6 depicts how a probing tip 122 can be removed from and reattached to the shaft 106. In this embodiment, the blade 108 is secured to the shaft using a resistance mechanism 110, which in this embodiment comprises a metal spring mechanism. The mechanical sensor 114 is wired to the blade 108 and relays the amount the blade 108 penetrates wood at each location. The probing tip 122 has a hole designed to allow the blade 108 to protrude out from the shaft 106.

Figure 7:
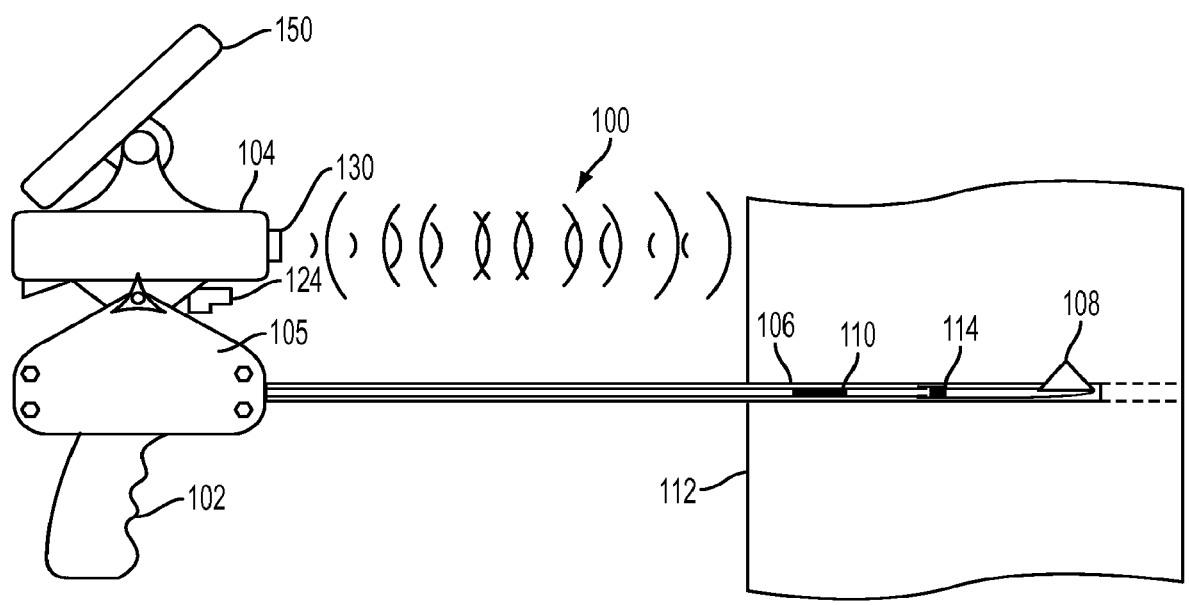

FIG. 7 depicts a side view of an exemplary device of an embodiment of the present invention in operation. The probing device 100 is shown inspecting the hardness of a wooden structure 112. The distance sensor 104 is powered on and then sends a sonar signal off the surface of the wooden structure 112, which is then reflected back and received by the distance sensor 104. The end of the shaft 106 closest to the blade 108 is inserted into a bored hole in the wooden structure 112. The distance sensor 104 determines the location of the blade 108 using a calculation based on the distance between the transmitter/receiver 130 of the distance sensor 104 and the wooden structure 112, the length of the shaft 106 up to the blade 108, and the angle between the distance sensor 104 and the shaft 106. The mechanical sensor 114, which is coupled to a resistance mechanism 110, measures the resistance to penetration applied to the blade 108 by the location in the wooden structure 112. The location and resistance to penetration data from the inspection are stored in the electronics unit 105, visually displayed on the device using visual display 150, and/or transmitted to a remote computing device, using the wireless transmitter 124. In this embodiment, the vertical handle 102 is not parallel to the shaft 106.

Figure 8:
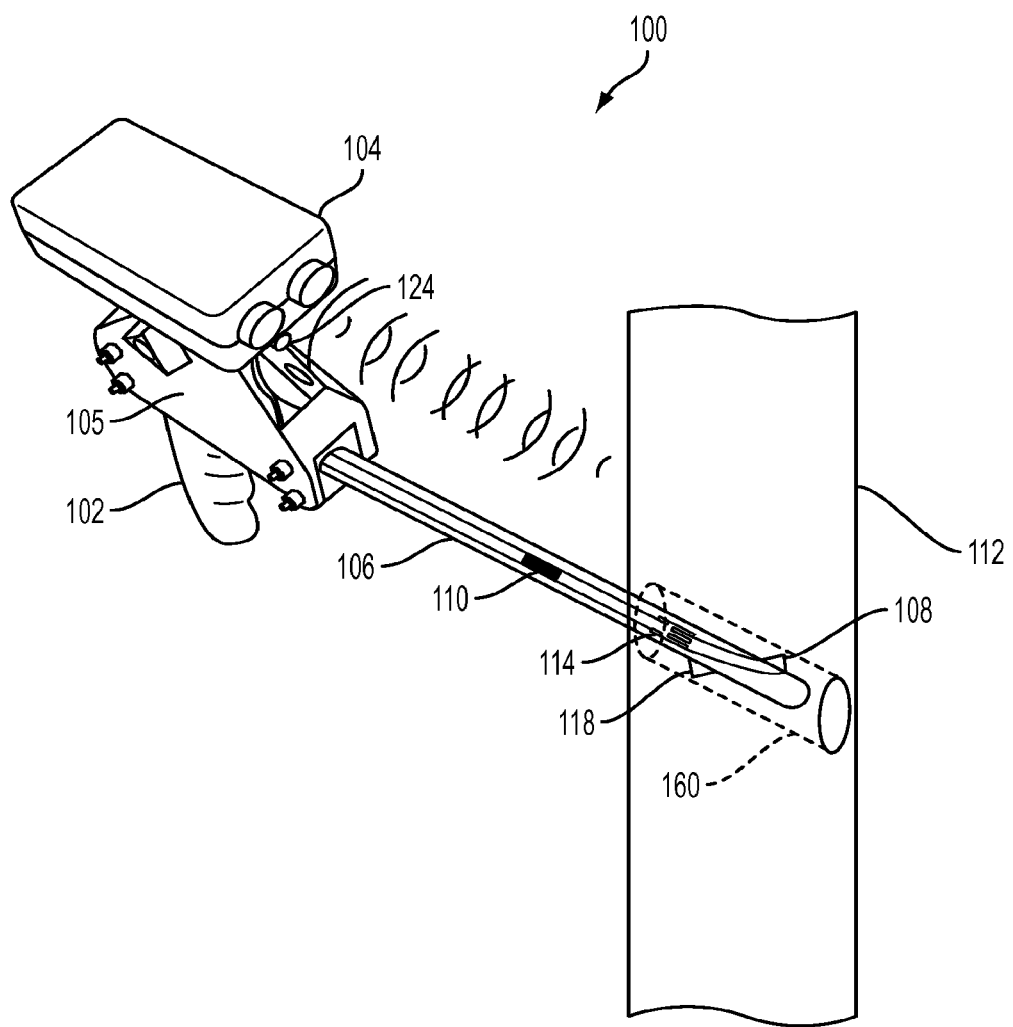

FIG. 8 depicts an angled view of an exemplary device of an embodiment of the present invention having two blades. When inserted into a bored hole, the distance sensor 104, in conjunction with a processor in the electronics unit 105, can determine the location of the blade 108, and the location of the second blade 118, within the wooden structure 112. Each blade is connected to a resistance mechanism 110 and a mechanical sensor 114. In this embodiment, the probing device 100 can obtain two sets of location and penetration resistance data simultaneously.

Figure 9:
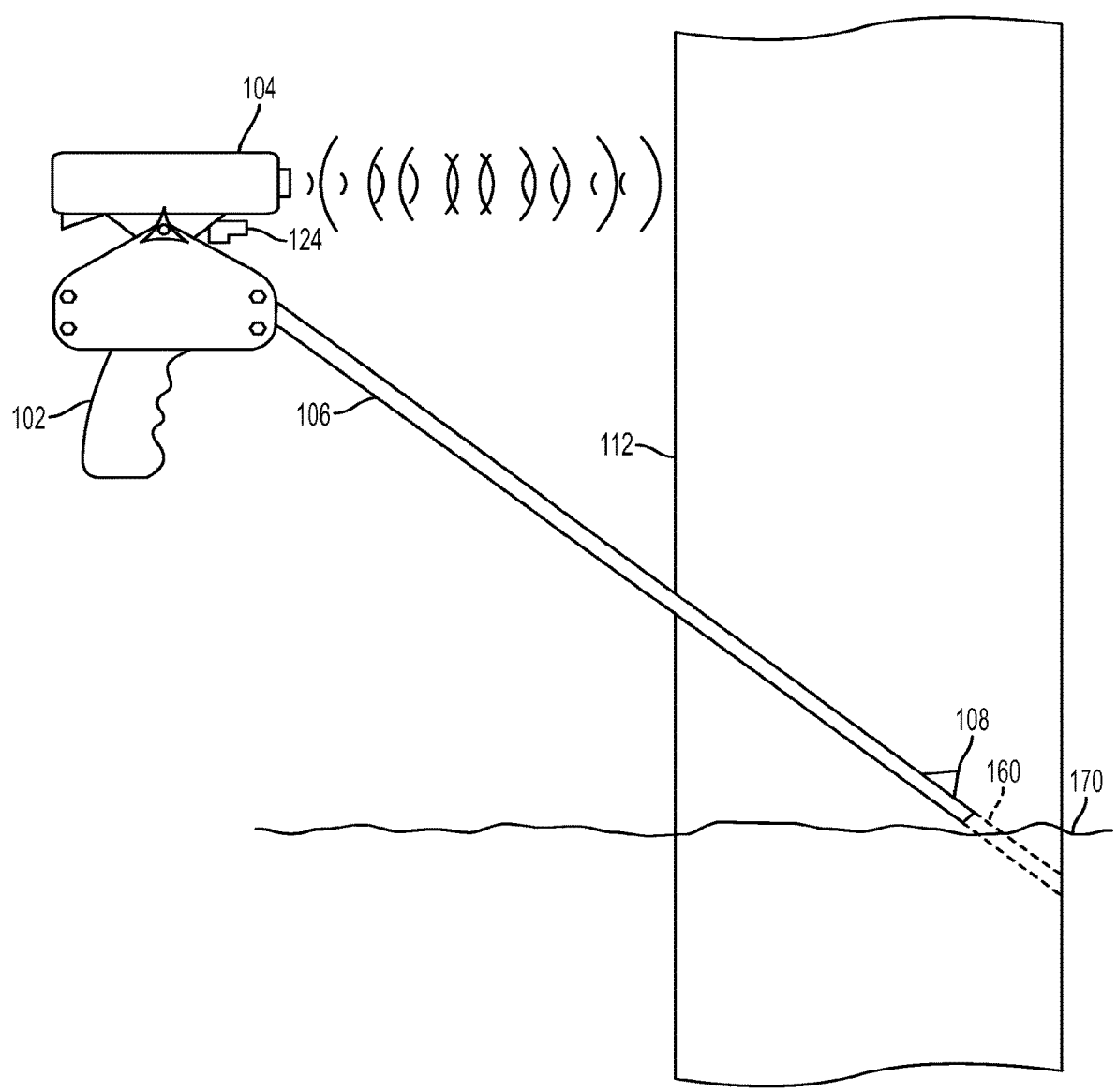

FIG. 9 depicts a distance sensor 104 at a non-zero angle to the shaft 106 of an embodiment of the present invention. This exemplary configuration may be useful in inspecting the hardness and condition of portions of a wooden structure 112 below the ground-line 170. The distance sensor 104 can calculate the location of the blade 108 within the wooden structure 112 using the distance provided by the sonar signal, the length of the shaft 106 up to the blade 108, and the angle between the sonar signal of the distance sensor 104 and the shaft 106.

Figure 10A:
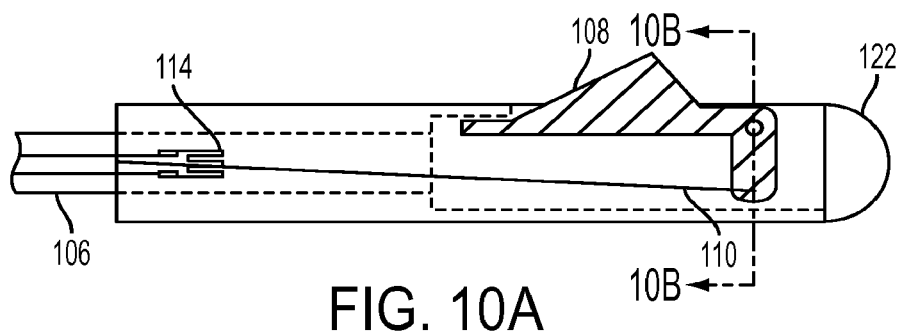
FIGS. 10A and 10B depict a spring-loaded blade protruding from a shaft of an exemplary device of an embodiment of the present invention.
Figure 10B:
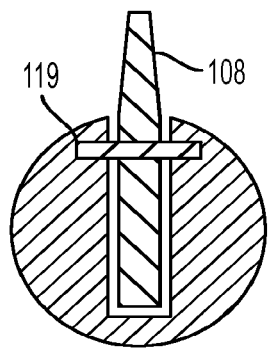

FIGS. 10A and 10B depict a blade 108 protruding from a shaft 106 of an exemplary device of an embodiment of the present invention. In FIG. 10A, the probing tip 122 end of the shaft 106 is shown. FIG. 10B shows a cross-sectional view of the area indicated as 10B in FIG. 10A viewed from the end of the probing tip 122. A pin 119, which can be a small metal elongated cylinder, is secured to the probing tip 122. The pin 119 slides through a fitted hole in the blade 108, such that the blade 108 can rotate about the pin 119. The resistance mechanism 110 is a spring-loaded mechanism, which, when connected to the blade 108 and tensioned, secures the blade 108 to the shaft 106 such that the blade 108 rotates upward and protrudes from the shaft 106. The metal wire of the resistance mechanism 110 is also connected to a mechanical sensor 114. When the blade 108 is inserted into a bored hole of a wooden structure, the blade 108 rotates down about the pin 119, for example when contacting portions of wood having sufficient hardness compared to a reference wood, or remains protruded, for example when contacting areas of significant decay, depending on the force provided by the resistance mechanism 110. The mechanical sensor 114 determines the amount of penetration of the blade 108 in the wood, by measuring, for example, the displacement value of the blade 108 compared to its fully protruded position.

Figure 11:
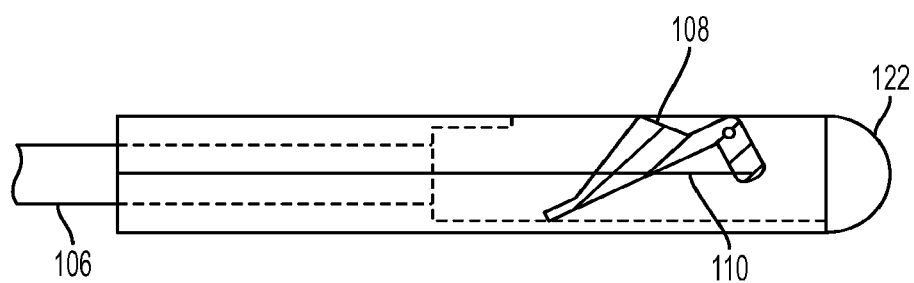

FIG. 11 depicts a blade 108 retracted into a probing tip 122 of a shaft 106 of an exemplary device of an embodiment of the present invention. The blade 108 in FIG. 11 is fully retracted into the shaft 106, which may occur for instance when the blade 108 contacts a portion of an inspection hole having the hardness of a reference wood. The mechanical sensor would then measure the displacement value or resistance to penetration, which in this example would correlate to a portion of wood having sufficient hardness compared to a reference wood.

Figure 12:
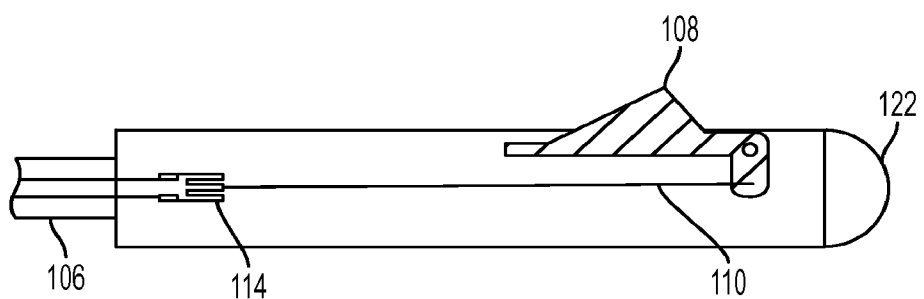

FIG. 12 depicts a mechanical sensor 114 connected to a spring-loaded blade 108 within the probing tip 122 of the shaft 106 of an exemplary device of an embodiment of the present invention. In this example, the mechanical sensor 114 is a displacement transducer, which, when connected to the resistance mechanism 110, can measure the amount the blade 108 penetrates wood. Both the mechanical sensor 114 and the resistance mechanism 110 are fitted within the probing tip 122 of the shaft 106.

Figure 13A:
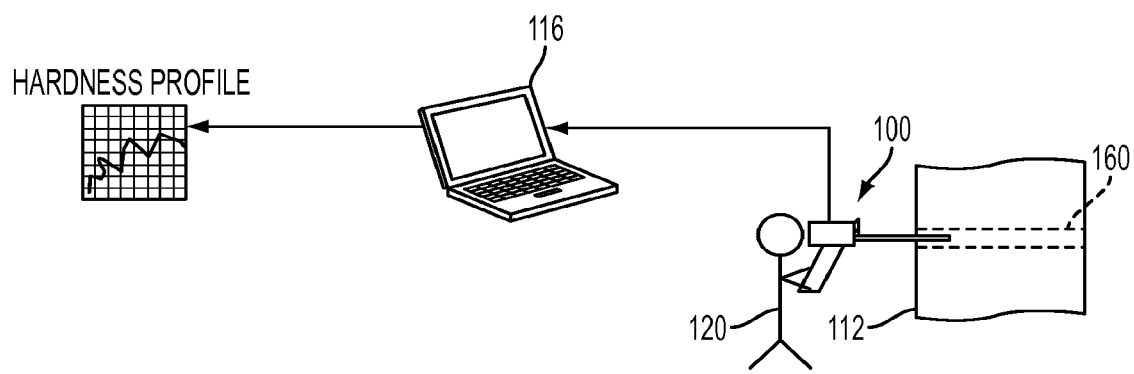
FIGS. 13A and 13B depict an exemplary system of an embodiment of the present invention for evaluating the hardness of a wooden structure.
Figure 13B:
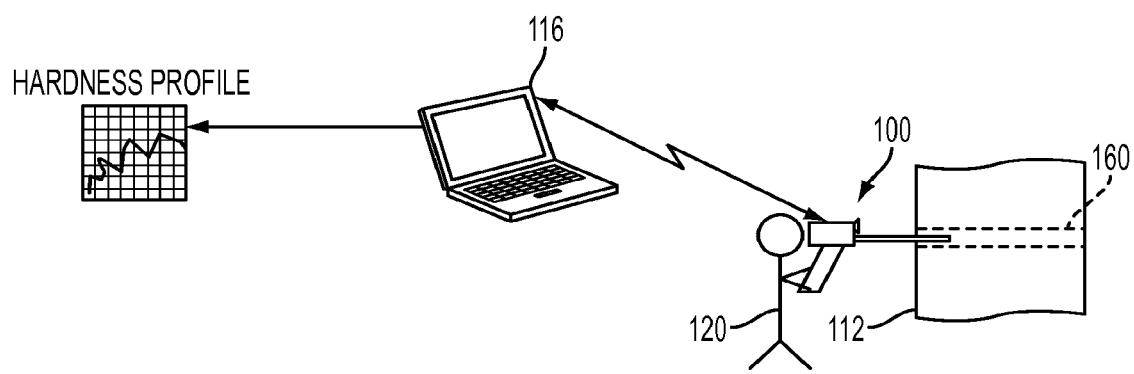

FIGS. 13A and 13B depict an exemplary system of an embodiment of the present invention for evaluating the hardness of a wooden structure. The system includes a probing device 100, a wooden structure 112, an operator 120, and a computing device 116. The wooden structure 112 includes an inspection hole 160, which may be pre-drilled or drilled by the operator 120 or other individual during the inspection. The probing device 100 then measures the amount that the blade is able to penetrate the wood when inserted into, and through the inspection hole 160. The data obtained by the probing device 100 is then transmitted to a computing device 116, via a physical connection or download as shown in FIG. 13A, or wirelessly as shown in FIG. 13B. The computing device 116 can then sort and analyze the data to provide a hardness profile of the wood surrounding the inspection hole 160, or multiple inspection holes, within the wooden structure 112, to determine whether the wooden structure 112 requires any immediate or future remedial treatment, reinforcement, or replacement.

Figure 16:
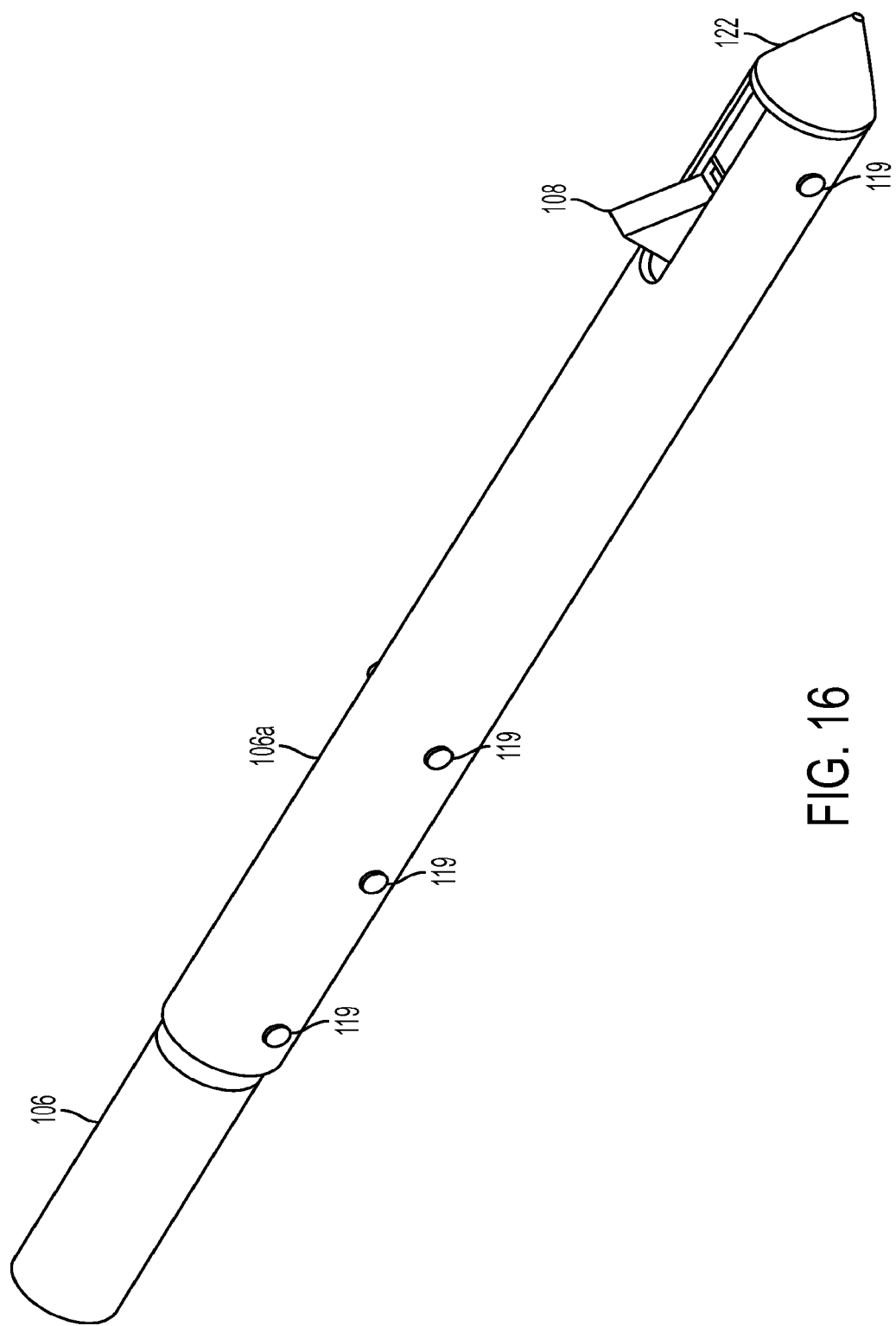
Figure 17:
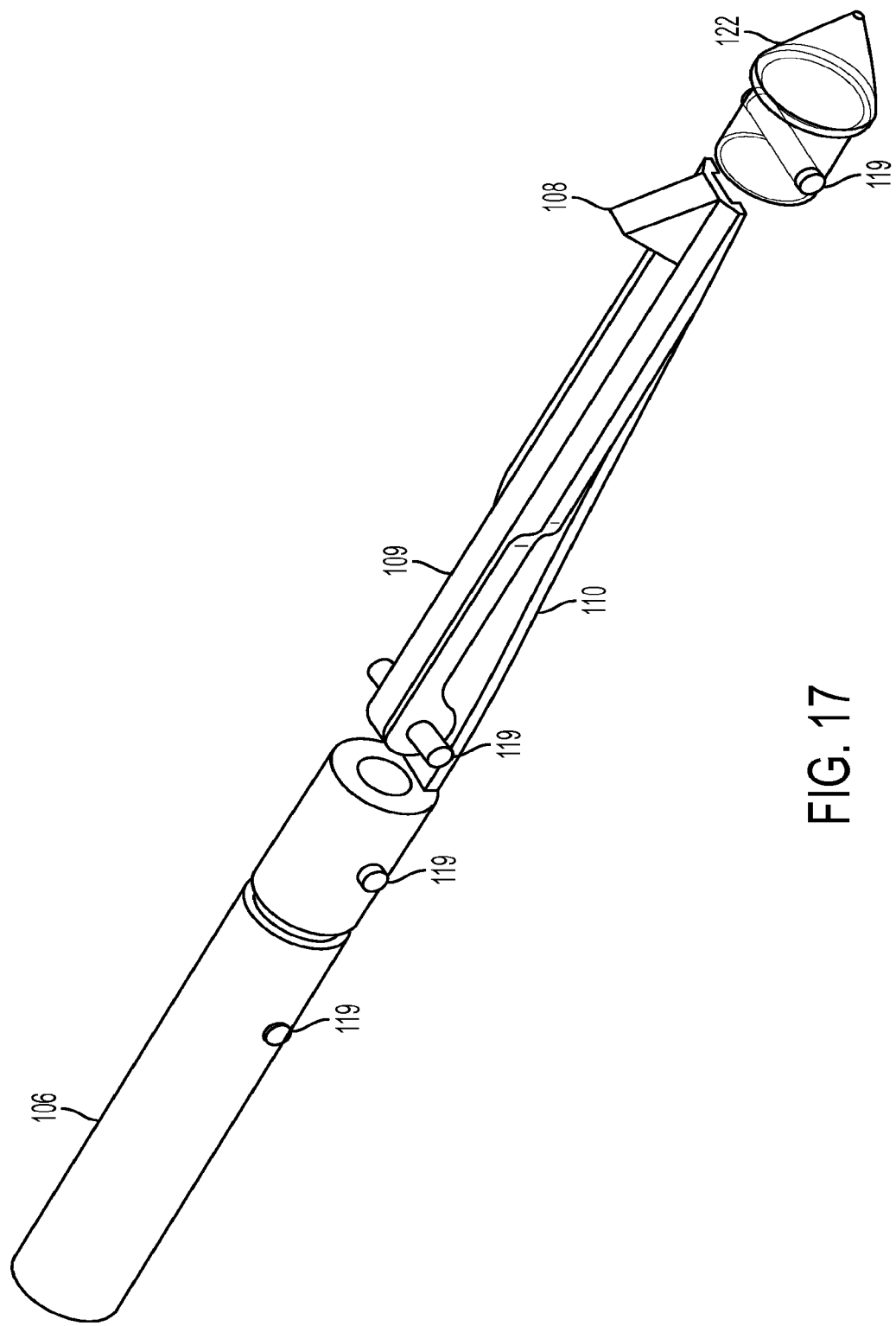
Figure 18:
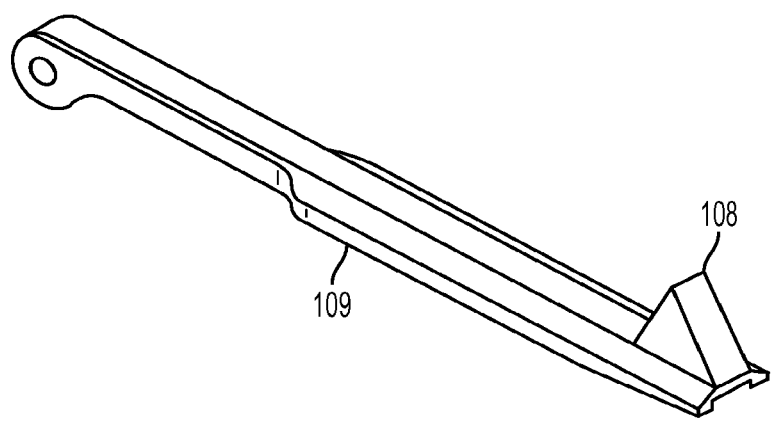
Figure 19:
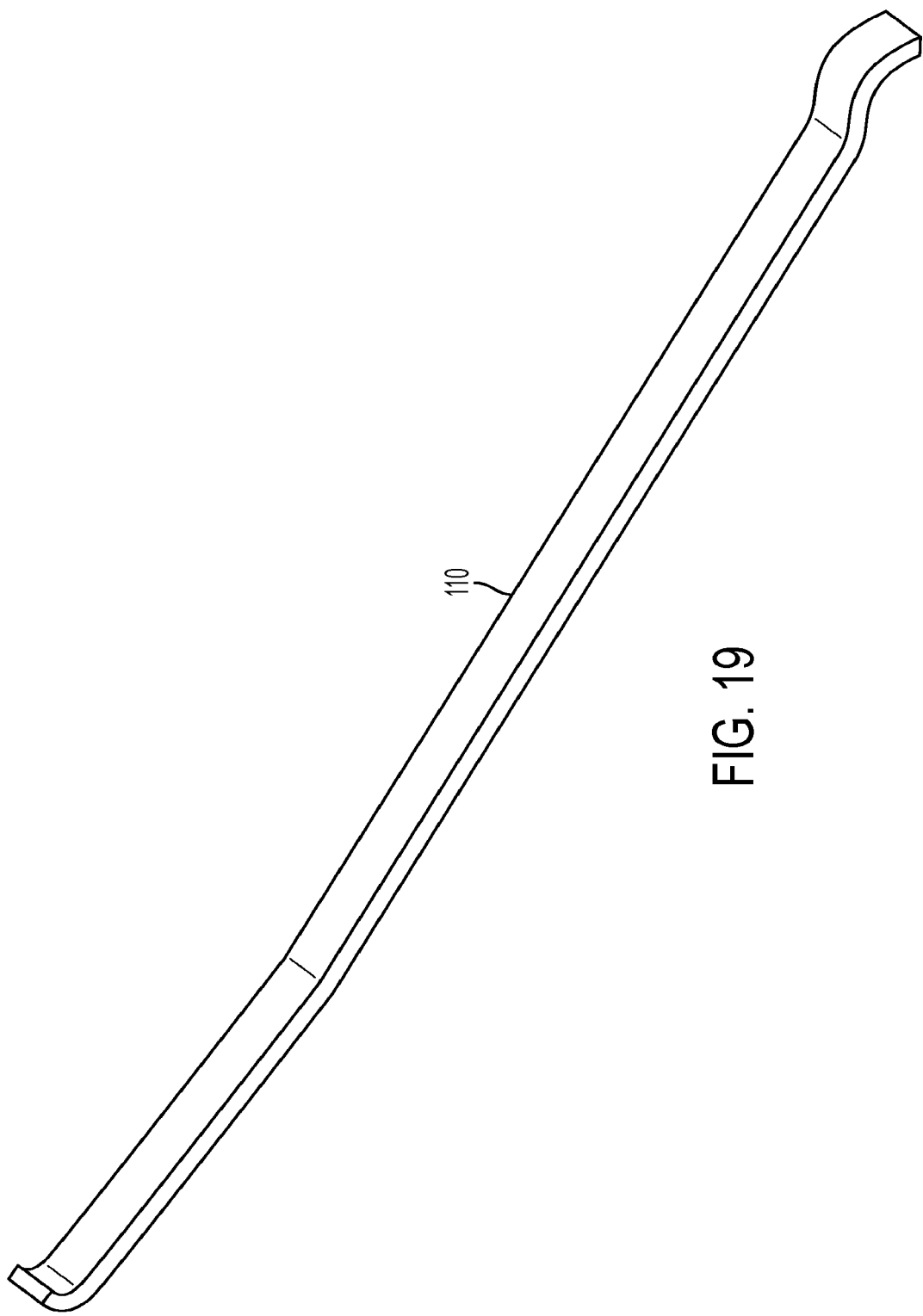

FIGS. 16-17 depict the assembly of one end of an exemplary device of the present invention. FIG. 16 shows an external view of the assembly, wherein the shaft 106 comprises a tube 106a and a probing tip 122. The probing tip 122, which has a conically shaped end, is secured to one end the tube 106a, and the other end of the tube 106a is secured to the substantial remainder of the shaft 106. The tube 106a fits over the blade 108 with an opening to allow the blade to protrude out from the shaft, and the probing tip 122 is adjacent to the blade. The probing tip 122 also has a slot (not depicted) for wood particles to be removed. In this embodiment, multiple pins 119 are used to secure components of the device together. FIG. 17 depicts the assembly shown in FIG. 16, wherein the tube 106a portion of the shaft 106 has been removed. The blade 108 is secured to a pivot arm 109, which is secured to the shaft by a pin 119 that slides through a fitted hole on the end of the pivot arm opposite the blade. The blade 108 and the pivot arm 109 sit atop a spring, which is the resistance mechanism 110 in this embodiment. In this assembly, when the blade 108 is inserted into a bored hole of a wooden structure, the blade 108 can retract into the shaft as the pivot arm 109 rotates down about a pin 119, for example when contacting portions of wood having sufficient hardness compared to a reference wood, or the blade 108 can remain protruded, for example when contacting areas of significant decay. The tension loaded into the spring can be adjusted to increase or decrease the amount of force necessary to partially and/or completely retract the blade 108 into the shaft, and thus help optimize the sensitivity of the measurement. FIG. 18 depicts a close-up of the blade 108 secured to the pivot arm 109, which will be positioned on top of and in contact with the spring depicted in FIG. 19.

Figure 20:
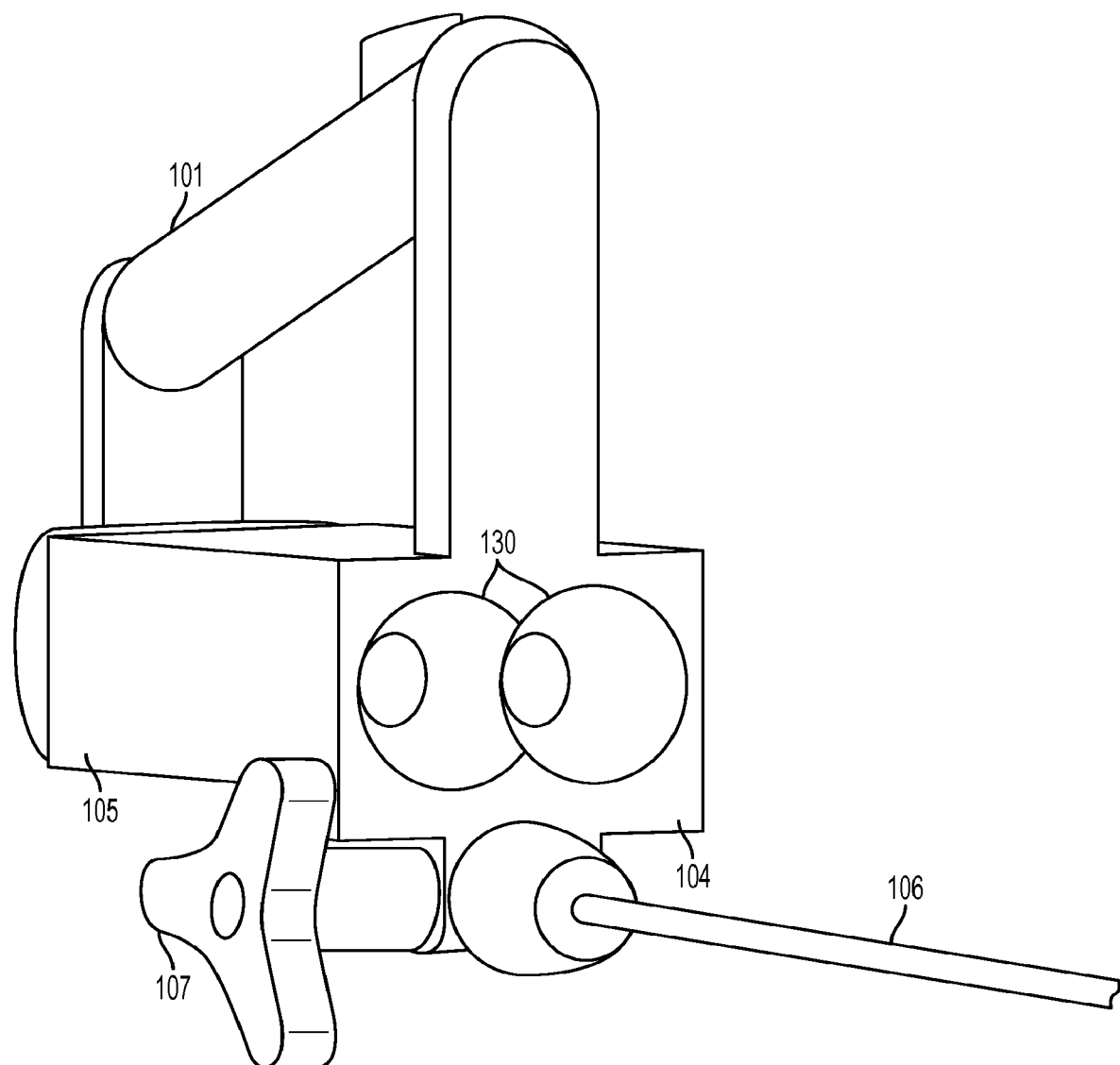
Figure 21:
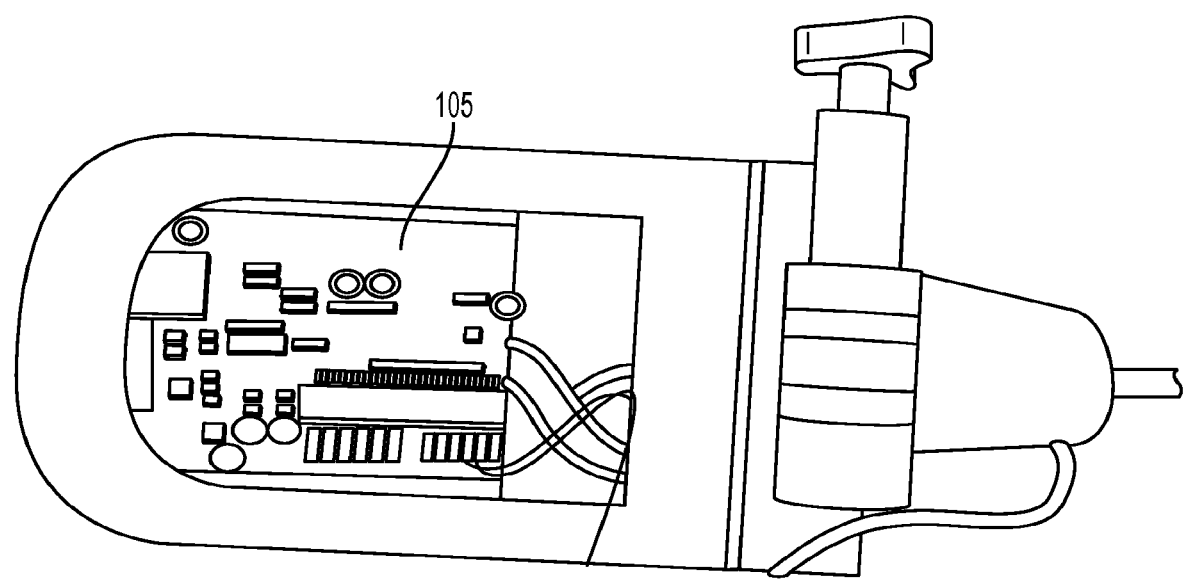

FIG. 20 depicts an end of an exemplary device of an embodiment of the present invention, wherein a distance sensor 104, a raised handle 101, an electronics unit 105 and a dial 107 are attached to the shaft 106. FIG. 21 depicts how the housing of the electronics unit 105 can be opened to allow electronics access, for example, by a field operator after inspecting a utility pole. The housing of the electronics unit 105 may be made of plastic, fiberglass, or more preferably metal, and in certain embodiments the housing and the raised handle 101 can be manufactured using 3-dimensional printing.

Figure 22:
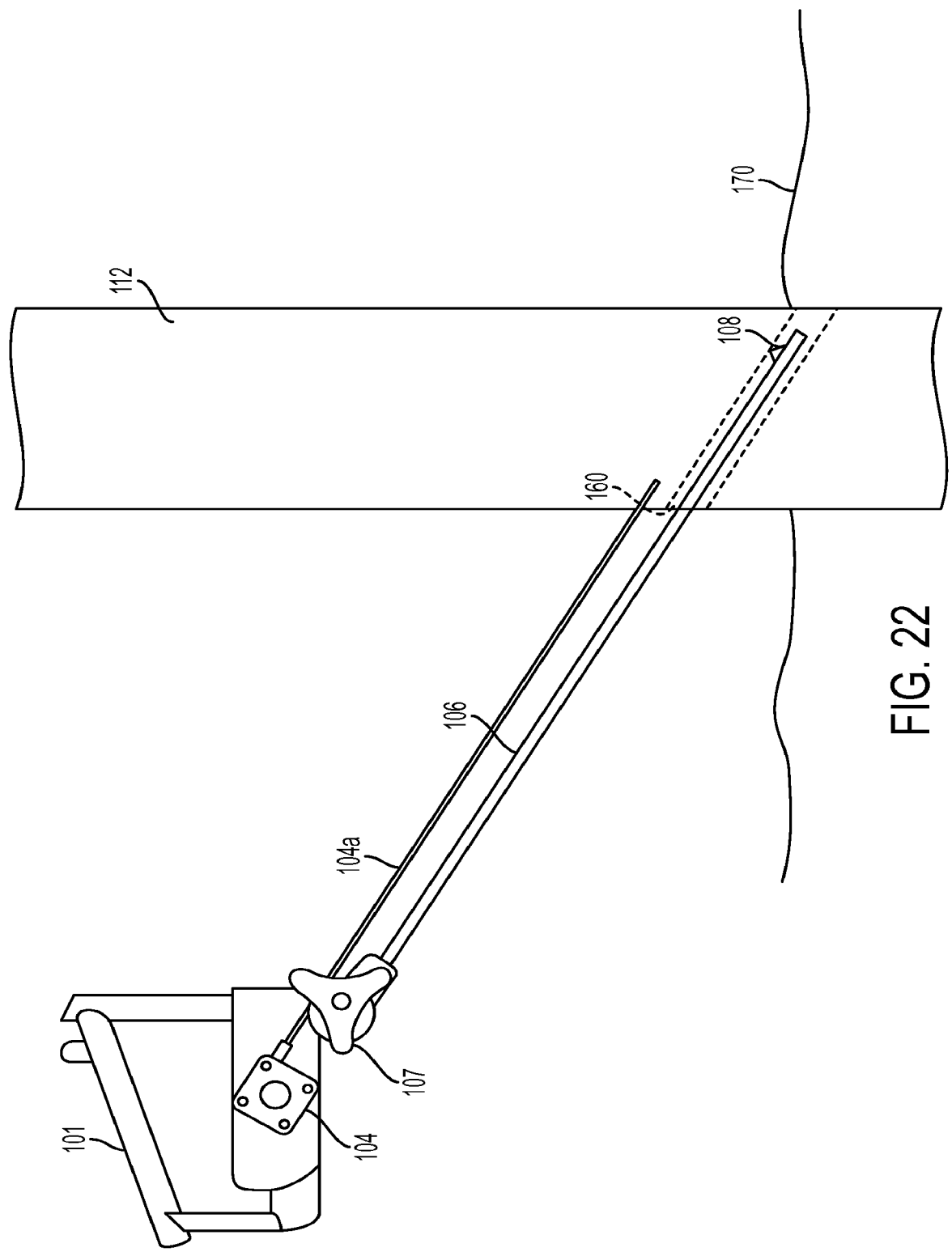

FIG. 22 depicts a side view of an exemplary device of an embodiment of the present invention, wherein the distance sensor 104 is a string potentiometer, and the shaft 106 is angled downward to inspect the area of a wooden structure 112 below ground-line 170. The angle of the shaft to the ground-line is measured using an inclinometer in this embodiment. The string potentiometer determines the distance that the blade 108 has traveled within the wooden structure 112 using a cable or string tethered to a stable support, for example, the wooden structure. As the blade 108 moves further into the structure, the corresponding movement of the cable produces a voltage range, which is converted from an analog signal, in this case variable voltage, to the digital output, in this case distance, using an analog-to-digital converter, and the digital output is recorded. Using the distance measured by the string potentiometer and the angle of the shaft measured by the inclinometer, the location of the blade 108 within the structure can be automatically determined. In preferred embodiments, the angle measured by the inclinometer is with respect to the horizontal plane, typically perpendicular to the vertical axis of the pole.

Figure 23:
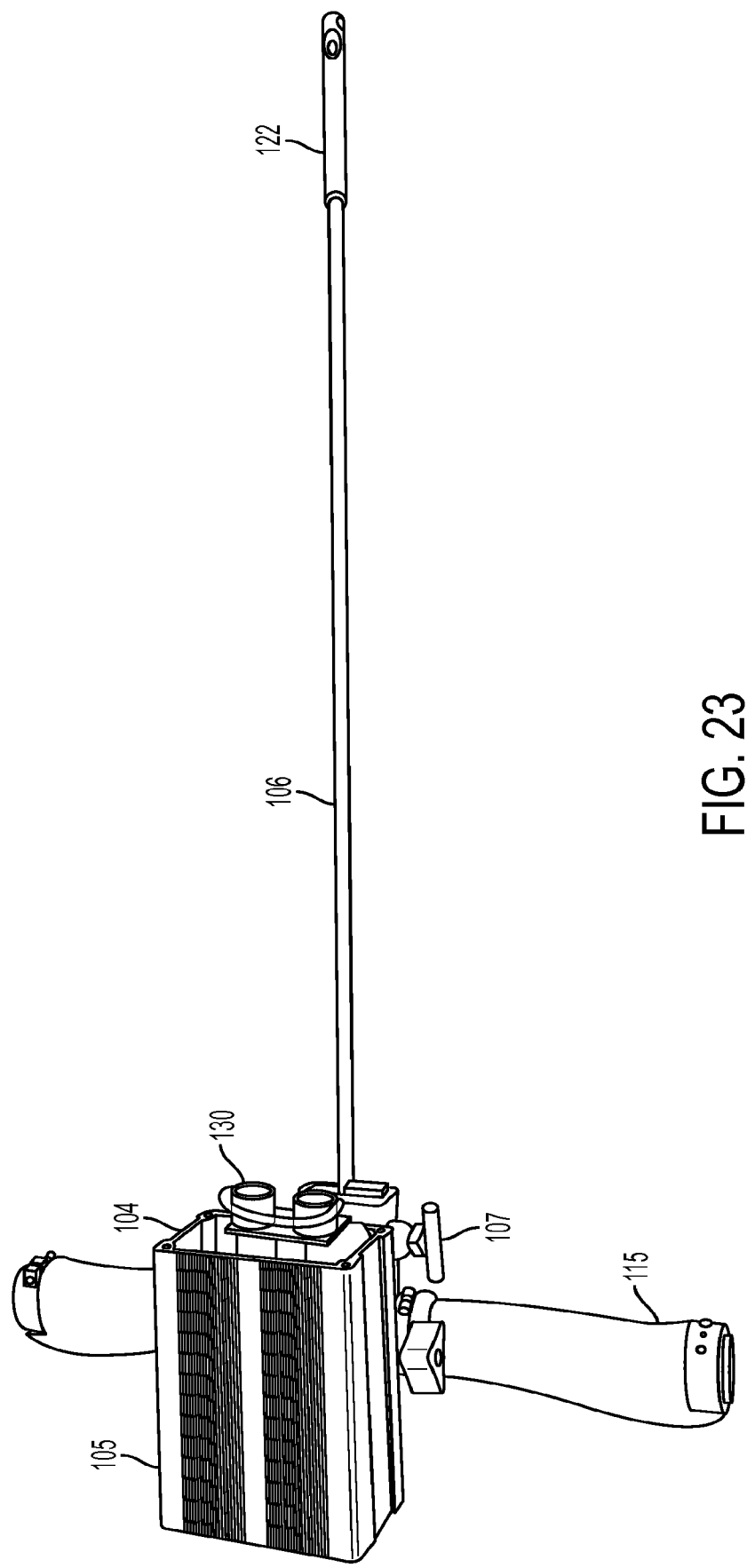

FIG. 23 depicts an overhead view of an exemplary device of an embodiment of the present invention, wherein the distance sensor 104 comprises a sonar instrument with two sound transmitters/receivers 130 facing in the direction of the shaft 106. The device further comprises an electronics unit 105 within a metal housing attached to the shaft 106. In this embodiment, the dual-grip handle 115 comprises two rubber grips, one on each side of the shaft 106, which permit a user to operate the device with two hands to ensure careful and stable insertion of the probing tip 122 into and through a hole in a wooden structure.

Figure 24:
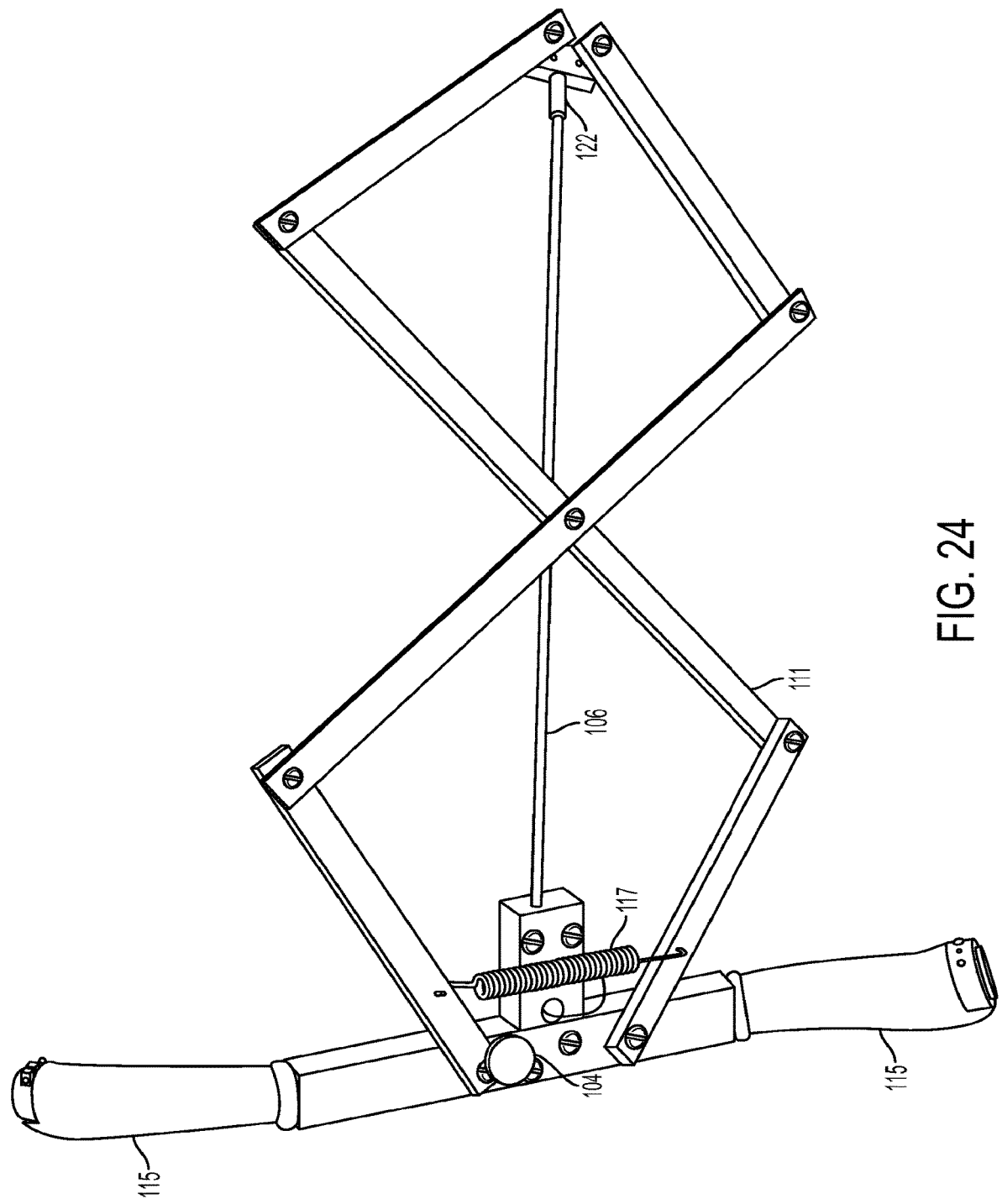

FIG. 24 depicts an overhead view of a distance sensor 104, which in this embodiment comprises a potentiometer connected to collapsible scissors 111. The collapsible scissors 111 are bolted to the base of the shaft 106 and expanded along the length of the shaft 106 up to the blade 108 (not depicted) using a spring 117. When the probing tip 122 of this embodiment is inserted into a wooden structure, the collapsible scissors 111 press against the surface of the wooden structure and fold back towards the base of the shaft 106 in a magnitude corresponding to the distance that the blade 108 has traveled into the wooden structure. A potentiometer is connected to the collapsible scissors 111. In this illustration, the potentiometer is connected to the end of the collapsible scissors 111 opposite the probing tip 122. The potentiometer rotates as the collapsible scissors 111 fold back towards the base of the shaft 106 and outputs a variable voltage corresponding to the degree of rotation. The variable voltage is then correlated to the distance or location of the blade 108 in the wooden structure. In this embodiment, a spring 117 is secured to the collapsible scissors 111 so that the collapsible scissors 111 fold back according to the movement of the shaft 106 into a hole in a wooden structure. The tension of the spring 117 is optimized to ensure accurate and repeatable distance or location measurements. As the probing tip 122 moves forward through a hole in a wooden structure, the collapsible scissors 111 are folded or compressed between the base of the shaft 106 and the wooden structure. An inclinometer (not depicted) may also be used in conjunction with the collapsible scissors 111 and the potentiometer to determine the location of the blade 108 within a wooden structure.

Figure 25:
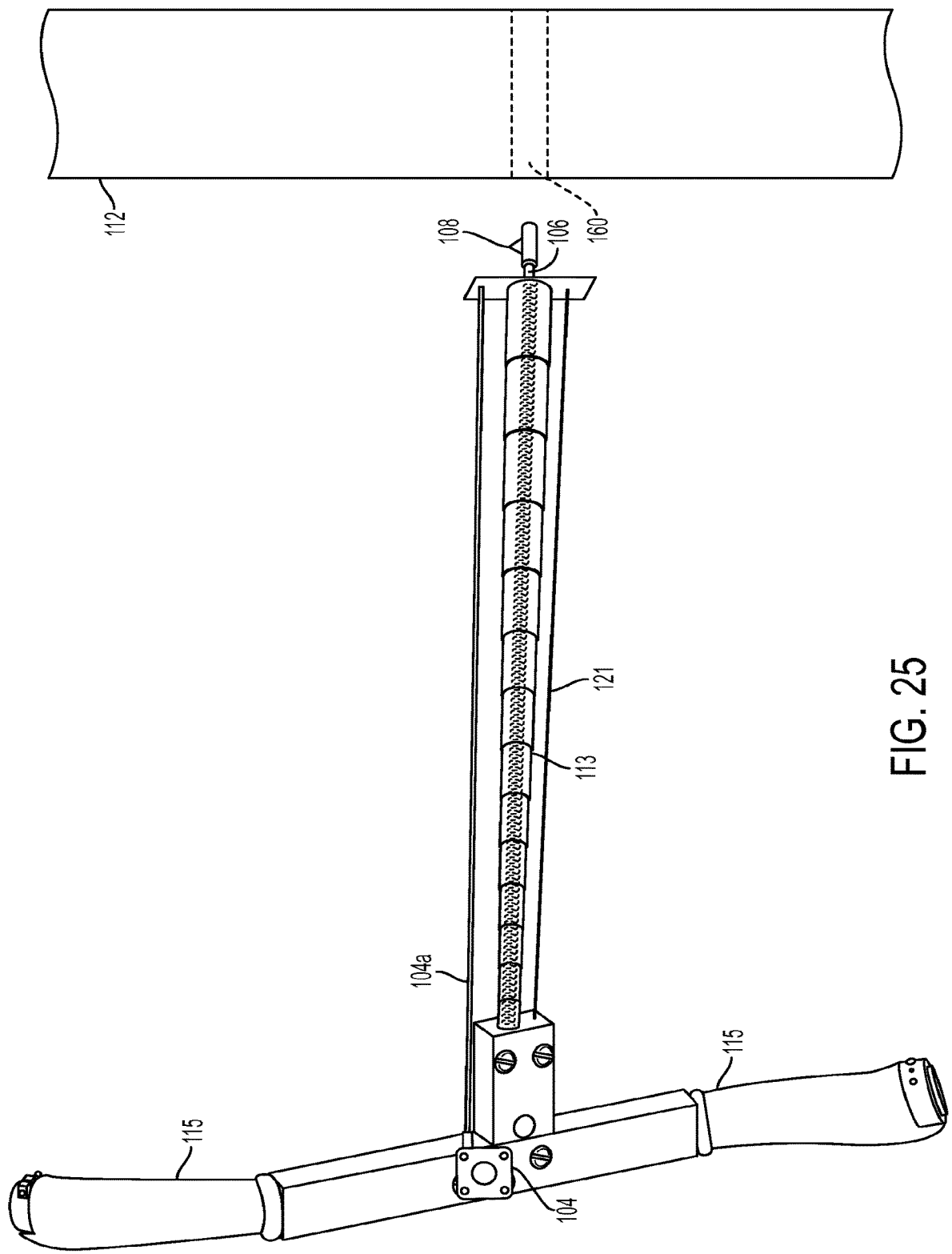

FIG. 25 depicts a side view of a distance sensor 104, which in this embodiment comprises a potentiometer and a compression sleeve 113 around the shaft 106. The compression sleeve 113 comprises an elongated spring affixed to the base of the shaft 106 and expanded along the length of the shaft 106 up to the blade 108. A stop wire 121 is secured to the dual-grip handle 115 and the end of the compression sleeve 113 closest to the blade 108 to prevent the compression sleeve 113 from extending beyond the end of the shaft 106. The potentiometer has a string or cable 104a attached to the end of the elongated spring closest to the blade 108, or attached to an encasement around the elongated spring. When the blade 108 is inserted into a hole 160 in a wooden structure 112, the compression sleeve 113 presses against the surface of the wooden structure 112 and compresses back towards the base of the shaft 106 in a magnitude corresponding to the distance that the blade 108 has traveled into the wooden structure. The string or cable 104a of the potentiometer recoils into the potentiometer as the compression sleeve 113 compresses back toward the base of the shaft 106. The potentiometer outputs a variable voltage corresponding to the movement of the string or cable 104a. The variable voltage is then correlated to the distance or location of the blade 108 in the wooden structure 112. The tension of the elongated spring in the compression sleeve 113 is optimized to ensure accurate and repeatable distance or location measurements. As the blade 108 and/or probing tip 122 (not depicted) moves forward through a hole 160 in a wooden structure 112, the compression sleeve 113 is compressed between the base of the shaft 106 and the wooden structure 112. An inclinometer (not depicted) may also be used in conjunction with the compression sleeve 113 and the string potentiometer to determine the location of the blade 108 within a wooden structure 112.

Overview of the Devices, Systems and Methods of the Invention

Changes in the hardness of a wooden structure are often indicative of the condition of that structure. For example, decay and decomposition of a wooden structure alter the structure of the wood and reduce the hardness of the structure, as compared to normal wood (for example, no decay and decomposition or mechanical damage). As used herein, the term "wooden structure" refers to a structure comprising wood, such as, but not limited to utility poles. Moisture penetration into a wooden structure (one indicator of pre-decay) also alters the hardness of the wooden structure, compared to a dry reference. The hardness of wood can be determined by measuring the wood's resistance to penetration.

The exemplary probing devices, systems, and methods of the instant invention may be used to evaluate the condition of a wooden structure, by measuring and recording a resistance to penetration by a blade, as quantified by for example a displacement value of a blade or the force applied to the blade by the surrounding wood, which helps indicate the hardness of wood at a given location. Hardness profiles can be assessed by conducting such measurements and recordings at various locations within the structure. The condition or strength of a wooden structure can be assessed by determining whether there are changes in hardness throughout the structure and/or whether the hardness at various locations within the structure differs compared to the hardness of reference wood. Wooden structures may on occasion comprise voids or pockets of air. The probes and devices of the present invention aid in the detection of voids or pockets in the wooden structures by noting the lack of hardness or density in a particular portion or region of the wood. The devices, systems, and methods of the present invention allow users to repeatedly and accurately profile the hardness and condition of wooden structures without the need for specialized and expensive drilling equipment.

The exemplary probing devices, systems, and methods of the instant invention may be used to detect distinct hardness conditions in wooden structure, including sound wood, incipient decay, and advanced decay. The term "incipient decay" as used herein refers to an early stage of the decay process where the wood fibers have begun to lose strength but the decay has not proceeded far enough to evidently soften or otherwise perceptibly reduce the hardness of the wood. Areas of incipient decay detected in wooden structures by the devices, systems, and methods of the present invention may be treated with fumigants, or other materials, compositions, or treatments, to stop or slow down infection or invasion by, for example, wood decay fungi, thereby extending the useful life of the wooden structure. A characteristic of incipient decay is that it can be arrested if the appropriate intervention or treatment is applied while the incipient decay is still in its early stages.

The term "hardness" as used herein refers to resistance to pressure, or resistance to penetration, or rigidity. For example, those of skill in the art will readily understand that resistance to penetration, or the displacement value of a blade based on a known applied force, among other measures, can be used to assess the hardness of wood. In addition, those of skill will understand that "hardness" may be assessed as a unitless measure of the relationship of resistance to pressure, resistance to penetration, displacement value of a blade, or other measure correlating resistance to pressure, or the rigidity of a wooden structure being inspected compared to a reference wood.

In an exemplary embodiment, the device 100 comprises a vertical handle 102, a distance sensor 104, a shaft 106, and a blade 108, as shown in FIG. 7. In certain embodiments, a resistance mechanism 110 is coupled to the blade 108 and a mechanical sensor 114 is coupled to the resistance mechanism 110 and the blade 108. In certain embodiments, the device is a handheld device. In an exemplary aspect, the device 100 is used to automatically profile the hardness, and as a result indicate the condition or strength, of a wooden structure 112. When introduced into a wooden structure 112, the blade 108 is capable of penetrating the surrounding wood. In certain embodiments, the amount that the blade 108 penetrates the wooden structure 112 is measured by a displacement value of the blade 108. In certain aspects, if the displacement value is lower than a predetermined "normal" displacement value, an operator can conclude that the hardness of the wood within a wooden structure 112 at the location examined is less than the hardness of a reference wood.

In another embodiment, the device 100 comprises a vertical handle 102, a distance sensor 104, a shaft 106, a blade 108, and a second blade 118, as shown in FIG. 8. In this embodiment, each blade is coupled to a resistance mechanism 110 and a mechanical sensor 114. In certain aspects, when inserted into a wooden structure 112, the embodiment shown in FIG. 8 is capable of measuring the hardness of wood at two locations within the structure simultaneously.

In certain aspects of the invention, the wooden structure 112 to be inspected is comprised primarily of wood. In certain exemplary aspects, the wooden structure 112 can consist of a utility pole, a piling, a beam, a board, a timber, or any other type of wooden structure. The wooden structure 112 can consist of Western red cedar, Douglas-fir, southern pine, lodgepole pine, or any other species of wood.

Shaft of the Device

In exemplary embodiments, the shaft 106 of the probing device 100 permits the blade 108 to be inserted into an inspection hole 160 in a wooden structure 112. The shaft 106 may be sufficiently long to allow inspection of underground portions of a wooden structure 112. When the shaft 106 is inserted into a wooden structure 112 at an angle toward the ground, as illustrated for example in FIG. 9, the shaft can probe portions of the structure underground, without the need to excavate the structure.

Preferably, the shaft 106 of the probing device is substantially rigid. The rigidity of the shaft 106 may be optimized, for example to help ensure accuracy and reliability of the measurements of a distance sensor 104 mounted to the shaft regarding the location of a blade 108 within a wooden structure 112. Further, a substantially rigid shaft can help the resistance mechanism protrude the blade 108 from the shaft, and the blade 108 to retract according to an applied force from within the structure.

The shaft 106 is preferably electrically non-conductive, but not necessarily so. Examples of material suitable for use as a shaft 106 include, but are not limited to, metals, carbon fiber, polyester, fiberglass, polyester impregnated with fiberglass, and the like. However, the shaft 106 could be comprised of a number of different materials, including electrically non-conductive or conductive materials. Any material that is resistant to both compression and tension would be suitable. For example, thermal and non-thermally formed plastics (PLA, ABS), or wood. In other words, any material that is strong enough to push the tip through the inspection hole 160 is suitable.

In certain embodiments, the shaft 106 may be substantially cylindrical in shape, having a diameter slightly smaller than the diameter of the inspection hole, for example having a diameter that is about 1% to about 10% less than the diameter of the inspection hole. In certain embodiments, the shaft 106 may have a diameter of between the range of about 0.1875 to about 0.375 inches, more preferably between the range of about 0.200 to about 0.300 inches. In certain embodiments, the diameter of the shaft 106 is sufficiently large to support the blade 108 and resistance mechanism 110, but small enough to be inserted into holes bored into a wooden structure 112 that are unlikely to harm the structural integrity of the wooden structure 112. Shafts having different diameters may be used to fit into various hole sizes (e.g., fume and inspection holes). In certain embodiments, the shaft 106 may be non-cylindrical and capable of being inserted into bored inspection holes having an appropriate diameter, as described above. In certain embodiments, the shaft 106 may be adjustable in length.

In embodiments of the present invention, the length of the shaft 106 may be sufficient to enable inspection of a wooden structure 112, such as a utility pole. In certain embodiments, the shaft 106 is sufficiently long to permit inspection of the portion of a utility pole underground, including the shell layers of the utility pole opposite the shell layers where the probing device is inserted into the utility pole. In certain embodiments, the shaft 106 is sufficiently long to enable inspection across the entire diameter of a utility pole at a 45 degree angle to the pole. As an example, the shaft may be about 24 to about 30 inches in length. In certain embodiments, the length of the shaft is adjustable. In certain embodiments, the shaft 106 may be designed to fold for ease of transport. In certain embodiments, the shaft 106 may be removable, or may comprise multiple removable sub-components. Embodiments of the device having a removable shaft can allow for different lengths or diameters of shafts to be used in the device.

The shaft 106 may comprise a probing tip 122 at the end of the shaft 106 nearest the blade 108, wherein the probing tip 122 surrounds one or more blades of the device. In certain embodiments, the probing tip 122 has a diameter slightly smaller than the diameter of the inspection hole 160, but slightly larger than the base of the shaft 106. For example, the probing tip 122 may have a diameter that is about 1% to 10% less than the diameter of the inspection hole, and about 1% to 10% greater than the diameter of the base of the shaft 106. In certain embodiments, the diameter of the probing tip 122 may be between the range of about 0.1875 to about 0.375 inches, more preferably between the range of about 0.250 to about 0.375 inches. In certain embodiments, the probing tip 122 may be a separate component from the shaft 106. In embodiments where the probing tip 122 collects debris in a bored hole, the probing tip 122 can have an additional slot for debris to exit. The probing tip 122 can be removable so that debris can be cleaned out or so that different attachments can be fastened to the tip of the shaft 106.

The shaft 106 may also comprise a tube 106a, as shown for example in FIG. 16. The tube 106a can be attached to the substantial remainder of the shaft using any attachment mechanism, including but not limited to a pin 119 or adhesive. The tube 106a portion of the shaft can be made of any material suitable to protect the components housed within the tube, including metal, carbon fiber, plastic, fiberglass, or other composite material. In certain embodiments, the shaft 106 may be attached to a handle, for example a raised handle 101, vertical handle 102, horizontal handle 103, or dual-grip handle 115. The handle may be designed to facilitate careful and reliable insertion of a probing device 100 into a wooden structure. In certain embodiments, the shaft 106 may include a latch or a safety cover to keep the blade retracted or covered when the device is not in use. The shaft 106 may also be hollow in certain embodiments.

Distance Sensor of the Device

In certain embodiments, the distance sensor 104 may be any sensor that allows the determination and/or recording of the location or depth of the blade 108 in the wooden structure 112. The distance sensor 104 includes but is not limited to mechanical, electrical, optical and acoustical sensors, and the like. In a preferred aspect, the distance sensor 104 is a potentiometer. For example, a string potentiometer, using a retractable cable, may be used as a distance sensor 104 in the present invention. As the cable moves, the potentiometer outputs a range of voltage that can be correlated to location, distance, or depth. The string potentiometer may be attached to the device at the handle or at the shaft 106, or encased in a collapsing housing. An analog-to-digital converter may be electrically connected to the distance sensor 104 to convert an analog signal (e.g., variable voltage) to a digital output (e.g., distance). For example, a string potentiometer may run through an ADS1115 Analog-to-Digital Converter (from Texas Instruments). As another example, a trellis or scissors potentiometer may be used as a distance sensor 104. In another aspect, the distance sensor 104 is a short-range sonar. For example, any short range sonar may be used as a distance sensor 104 in the present invention. An acoustic reflector (not depicted) may also be attached to the surface of the wooden structure.

In certain aspects of the invention, the distance sensor 104 is mounted on the handle or the shaft 106 of the probing device 100. In aspects of the present invention, the distance sensor 104 can consist of, for example, a short-range sonar, a laser, a short-range radar, or any other type of non-contact or contact distance sensor 104. In certain aspects, the distance sensor 104 is a short-range sonar which transmits a pulse of sound (also known as a "ping") from an acoustical transmit/receive array or an external transducer. The ping reflects off the surface of the wooden structure 112 and is received by the short-range sonar distance sensor 104. The distance sensor 104 then uses the speed of the transmitted ping and the elapsed time between the transmission and receipt of the ping to calculate the distance between the sensor 104 and the face of the wooden structure 112.

In aspects of the invention, as illustrated in FIG. 9, the distance sensor 104, for example a short-range sonar, can be oriented from about a 45 degree angle to about a 90 degree angle from the face of the wooden structure 112 while still receiving a sufficient return signal from the transmitted ping to provide the sensor 104 with an accurate distance reading.

In this way, the probing device 100 can be inserted into a wooden structure 112 to inspect the portions of the structure underground, including the shell of the structure underground. In certain embodiments, the angle is adjustable between about 0 and about 45 degrees; in further embodiments, the angle is adjustable between about 0 and about 90 degrees. In certain embodiments, the probing device comprises an inclinometer (not depicted). The inclinometer can be used, for example, to record the angle of the sonar to the shaft, record the angle of a bored hole to the ground, and/or to keep the sonar (or any other distance sensor) level.

In certain preferred aspects of the invention, as illustrated in FIG. 22, the distance sensor 104 comprises a potentiometer, more preferably a string potentiometer, which measures the distance of the blade within a wooden structure. For example, a SP1 50 string potentiometer (from Celesco) may be used as a distance sensor 104 in the present invention. In a preferred embodiment, the probing device also comprises an inclinometer (not depicted). The inclinometer can be used, for example, to record the angle of the string potentiometer to the shaft 106, record the angle of a bored hole 160 to the ground-line 170, and/or to keep the string potentiometer level. In a preferred embodiment, the inclinometer records the angle of the bored hole 160 to the ground-line 170, which, in conjunction with the distance or depth recorded by the potentiometer, can be used to determine the location of the blade 106 within the wooden structure 112. For example, the inclinometer may be an MMA7455 Digital Acceleration Title Angle Sensor Module (Freescale Semiconductor).

In certain embodiments of the invention, the distance sensor 104 comprises collapsible scissors 111 and a potentiometer. An example of this embodiment is illustrated in FIG. 24. The collapsible scissors 111 are expanded along the length of the shaft 106 with a spring 117. The collapsible scissors 111 collapse into the base of the shaft 106 when the probing tip 122 of this embodiment is inserted into a wooden structure and the collapsible scissors 111 are pressed against the surface of the wooden structure. The magnitude that the collapsible scissors 111 collapse or fold back toward the base of the shaft 106 can be measured by a rotating potentiometer that produces variable voltage. The variable voltage is then correlated to the distance or location of the blade 108 in the wooden structure, for example using an electronics unit and/or computing device attached to or remote from the device. An inclinometer (not depicted) may also be used in conjunction with the collapsible scissors 111 and the potentiometer to determine the location of the blade 108 within a wooden structure.

In certain embodiments of the invention, the distance sensor 104 comprises a potentiometer connected to a compression sleeve 113 around the shaft 106. An example of this embodiment is illustrated in FIG. 25. The compression sleeve 113 includes an elongated spring that expands along the length of the shaft 106 up to the blade 108. A potentiometer with a string or cable 104a is attached to the end of the elongated spring closest to the blade 108, or elsewhere along the compression sleeve 113. When the blade 108 is inserted into a hole 160 in a wooden structure 112, the compression sleeve 113 presses against the surface of the wooden structure 112 and compresses back towards the base of the shaft 106. The magnitude that the compression sleeve 112 compresses is measured by the string potentiometer, which produces a variable voltage. The variable voltage is then correlated to the distance or location of the blade 108 in the wooden structure, for example using an electronics unit and/or computing device attached to or remote from the device. An inclinometer (not depicted) may also be used in conjunction with the compression sleeve 113 and the string potentiometer to determine the location of the blade 108 within a wooden structure 112. A stop wire 121 is secured to the dual-grip handle 115 and to the end of the compression sleeve 113 closest to the blade 108. The length of the stop wire 121 should be sufficient to prevent the compression sleeve 113 from extending beyond the end of the shaft 106. The stop wire 121 may comprise, for example a string, cable, or wire and may be metal or non-metal.

Blade of the Device

In exemplary embodiments, the blade 108 of the probing device 100 is designed to ride along the inside of a bore hole within a wooden structure 112. When the shaft 106 of the probing device rides along an inspection hole 160, the blade 108 is capable of retracting in response to the force being applied by the wood within the structure surrounding the blade, resulting in a displacement value of the blade. In one aspect of the present invention, the blade 108 is attached to the end of the shaft 106 opposite the handle. In another aspect of the present invention, the blade is attached to the end of the shaft opposite the distance sensor 104. In certain embodiments, the blade 108 is attached to the shaft 106 using a pivot arm 109 and a pin 119 that permit the blade to retract into the shaft.

In certain embodiments, in decayed or decomposed portions of a wooden structure 112, or prior to insertion into a wooden structure 112, the blade 108 is able to penetrate the wood and does not retract into the shaft, as shown in FIGS. 10A-10B. In other embodiments, in portions of a wooden structure 112 having a hardness essentially the same as normal wood, the blade 108 does not penetrate the wood and retracts into the shaft, as illustrated in FIG. 11. In aspects of the present invention, the blade 108 partially penetrates the wood, and therefore partially retracts into the shaft 106.

In one aspect of the invention, the blade 108 is sized so that the blade can retract, either partially or more preferably completely, into the shaft 106. In one aspect, the blade 108 has a height substantially equal to the diameter of the shaft 106. In another aspect, the blade 108 has a height substantially equal to the diameter of the probing tip 122. In certain embodiments, the blade 108 has a height in the range of about 0.1875 to about 0.375. In another aspect, the blade has a length that is greater than its height. In certain embodiments, the blade 108 is bi-directional, such that the blade can provide hardness measurements as the device is being inserted into a wooden structure and as the device is being removed from a wooden structure. In bi-directional embodiments of the blade, preferably the length of the blade 108 is about twice the height of the blade 108. However, a blade 108 may be of any size suitable for minimally-invasive inspection of a wooden structure 112.

In certain aspects, when coupled to a resistance mechanism 110, the blade 108 is sufficiently sharp to penetrate portions of the wood within a structure having lower hardness compared to normal wood. In certain aspects, when coupled to a resistance mechanism 110, the blade 108 does not penetrate portions of the wood within a structure having a hardness essentially the same as normal wood. In certain aspects, a user may choose a sharper or duller blade 108 depending on the desired sensitivity in determining hardness variances in a wooden structure.

In certain preferred embodiments, the blade 108 comprises metal. For example, the blade 108 may comprise aluminum, stainless steel, alloy steel, spring steel or tool steel. In certain alternative embodiments, the blade 108 comprises tool ceramic, such as, for example zirconium dioxide, or carbide. Those of skill in the art will understand that any material, or combination of materials, may be used for the blade 108, such that the blade is capable of penetrating portions of wood having decreased hardness compared to normal wood.

In certain embodiments, the blade 108 has a sharp tip capable of penetrating a wooden structure. In certain embodiments, the blade 108 may be any shape having a sharp tip when protruded from the shaft 106 of the probing device 100. In certain embodiments, the portion of the blade 108 protruding from the shaft 106 is substantially triangular in shape. Preferably, the portion of the blade that protrudes from the shaft is substantially triangular, as illustrated in FIGS. 10A and 10B and FIGS. 16-18.

In one aspect of the invention, the blade 108 protrudes from the shaft 106 at a non-zero angle to the shaft. In certain embodiments, the blade 108 protrudes from the shaft 106 at an angle between about 30 degrees and about 90 degrees to the shaft or, between about 45 degrees and about 90 degrees to the shaft. In certain embodiments, the blade 108 protrudes from the shaft 106 at an angle of about 90 degrees to the shaft.

In certain embodiments, the probing device 100 comprises more than one blade. For example, the probing device may comprise a first blade 108 attached to the end of the shaft 106 opposite the vertical handle 102, and a second blade 118 attached to the shaft between the vertical handle 102 and the first blade 108, as illustrated in FIG. 8.

Resistance Mechanism of the Device

In embodiments of the invention, the resistance mechanism 110 may be any component, or combination of components that, when coupled to the blade 108, protrude the blade 108 from the shaft 106 of the probing device 100 by applying a force (e.g., pulling or pushing) to the blade. The resistance mechanism 110 allows the blade 108 to retract into the shaft 106, partially or completely, in response to an external force on the blade 108 opposite to and greater than the force provided by the resistance mechanism on the blade 108. In certain embodiments, the resistance mechanism 110 comprises a tension system. In certain aspects, the force provided by the resistance mechanism 110 can be adjusted.

In one preferred aspect, the resistance mechanism 110 comprises a spring-loaded mechanism, as illustrated in FIGS. 10A and 11. In another aspect, the resistance mechanism 110 comprises a pin that permits the blade 108 to rotate upward, and protrude from the shaft 106, when an external force is applied insufficient to counter the force of the resistance mechanism 110, for example when the blade 108 encounters decayed wood. Conversely, the resistance mechanism 110 permits the blade 108 to rotate downward, and retract back into the shaft 106, when a sufficient force is applied to counter the force of the resistance mechanism 110, for example when the blade 108 encounters normal wood. As an example, prior to insertion into a bored hole in a wooden structure 112 having normal hardness, an exemplary spring-loaded resistance mechanism 110, illustrated in FIG. 10A, protrudes the blade 108 from the shaft 106. When inserted into a bored hole in a wooden structure 112 having normal hardness, the spring-loaded blade retracts into the shaft, as shown in FIG. 11, because the portion of the wood surrounding the blade has sufficient hardness to push the blade 108 back into the shaft 106.

In other embodiments of the invention, the resistance mechanism 110 may comprise a wire-tensioned system, a hydraulic piston system, a spring system, a viscoelastic material, a torsion system, or an electro-magnetic or electro-mechanical system, such as a motor or solenoid. However, any resistance mechanism 110, or combination of resistance mechanisms, may be used that can protrude one or more blades from the shaft 106, and can allow the one or more blades to retract when pressed against a wooden structure having normal hardness.

Mechanical Sensor of the Device

In embodiments of the present invention, the mechanical sensor 114 of the probing device 100 can provide measurements corresponding to the hardness of the wood surrounding the blade 108 within a wooden structure 112. In certain embodiments, the mechanical sensor 114 is coupled to the resistance mechanism 110 and the blade 108, and measures the force applied on the blade 108 by portions of wood within a structure. In certain embodiments, the mechanical sensor 114 is coupled to the resistance mechanism 110 and the blade 108 and measures the amount the blade 108 penetrates the surrounding wood within the structure, resulting in a displacement value of the blade. In certain embodiments, when the value measured by the mechanical sensor 114, whether that value is the force applied, the displacement value, or another measure correlating to hardness of the surrounding wood, is different from the expected value from normal wood, the mechanical sensor 114 can indicate areas of damage or decay, among other potential irregularities, within the structure.

In certain embodiments, the mechanical sensor 114 is attached to the shaft 106 of the probing device, as illustrated in FIG. 12. In certain embodiments, the mechanical sensor 114 is attached to the end of the shaft 106 of the device near the blade 108. In certain embodiments, the mechanical sensor 114 is attached to the end of the shaft 106 opposite the blade 108. The mechanical sensor 114 may be attached to the shaft 106, or be remote from the shaft 106, in any way such that the mechanical sensor 114 can measure the force applied on the blade 108, the distance the blade 108 penetrates the structure, and/or any other mechanical measure correlating to hardness of the wood contacting the blade 108.

In an exemplary embodiment, the mechanical sensor 114 comprises a linear position or displacement transducer with an extensible wire rope, wherein the wire rope is attached to the blade 108, as illustrated in FIG. 12. In this embodiment, the mechanical sensor 114 can measure the displacement value of the blade 108 when inserted into a bored hole in a wooden structure 112, by measuring displacement of the wire-rope. The mechanical measurement is converted to an electrical signal, which can be transmitted to a computing device 116 and processed to analyze the hardness of the wooden structure. The displacement value may be measured at various locations within the wooden structure 112, correlated to the hardness of wood to create a hardness profile of the wooden structure, and compared to the hardness profile of normal wood.

In certain embodiments of the invention, the mechanical sensor 114 may comprise a displacement transducer or a force transducer capable of measuring a displacement value or force value on the blade caused by the wooden structure 112. In certain embodiments, the mechanical sensor 114 converts the mechanical measurement into an electric signal that may be transmitted to a computing device 116 for further processing. In certain embodiments, the mechanical sensor 114 may comprise a strain gauge, load cell, potentiometer, flex sensor, or pressure sensor. In certain aspects, a user may select a particular mechanical sensor 114 based on compatibility with the selected resistance mechanism 110. For example, an Omega Engineering KFH-3-350-C1-11L3M3R strain gauge may be used as a mechanical sensor 114 in the present invention. An analog-to-digital converter may be electrically connected to the mechanical sensor 114 to convert an analog signal to a digital output. In a preferred embodiment, the mechanical sensor 114 is a strain gauge that runs through an HX711 24-Bit Analog-to-Digital Converter (from Avia Semiconductor).

In certain embodiments, the device includes other sensors that may be helpful to those of skill in the art in assessing a wooden structure, including but not limited to one or more moisture content sensors. In certain embodiments, one or more sensors, including passive or active acoustic sensors, galvanic sensors, resistive sensors, capacitive sensors, or gas sensors to detect insect respiration or decay outgassing in addition to the mechanical sensor, are attached to the shaft 106 of the probing device 100.

Methods and Systems for Evaluating a Wooden Structure

In aspects of the invention, a blade 108, coupled to a resistance mechanism 110 and a mechanical sensor 114, is inserted into a hole in a wooden structure 112 to gather data about the internal hardness of that structure. The hole may be pre-drilled, or may be bored or drilled by the personnel conducting the inspection of the structure, by using a drill or a borer, for example. In some aspects of the invention, the blade 108 is inserted into a pre-drilled hole to avoid drilling new holes that may further compromise the integrity of the structure. In other aspects of the invention, the personnel conducting the inspection of the structure may choose to drill or bore a new hole in the structure to ensure that the wood surrounding the entrance of the hole is healthy, non-decayed wood that provides an accurate hardness for the measurements. In these aspects, the personnel may penetrate the exterior of the wooden structure with the drill or bore above the ground line of wooden structure, and then angle the drill or bore downwards so that at least a portion of the inspection hole in the interior of structure is located below the ground-line of the structure, which is a prime location for decay. In aspects of the invention, the inspection hole may be sufficiently small to permit the blade 108 to ride along the bore hole and retract according to the hardness of the wood surrounding the blade. For example, the diameter of the inspection hole may be essentially the same as, but not less than, the diameter of the shaft 106 of the probing device 100.

Figure 15:
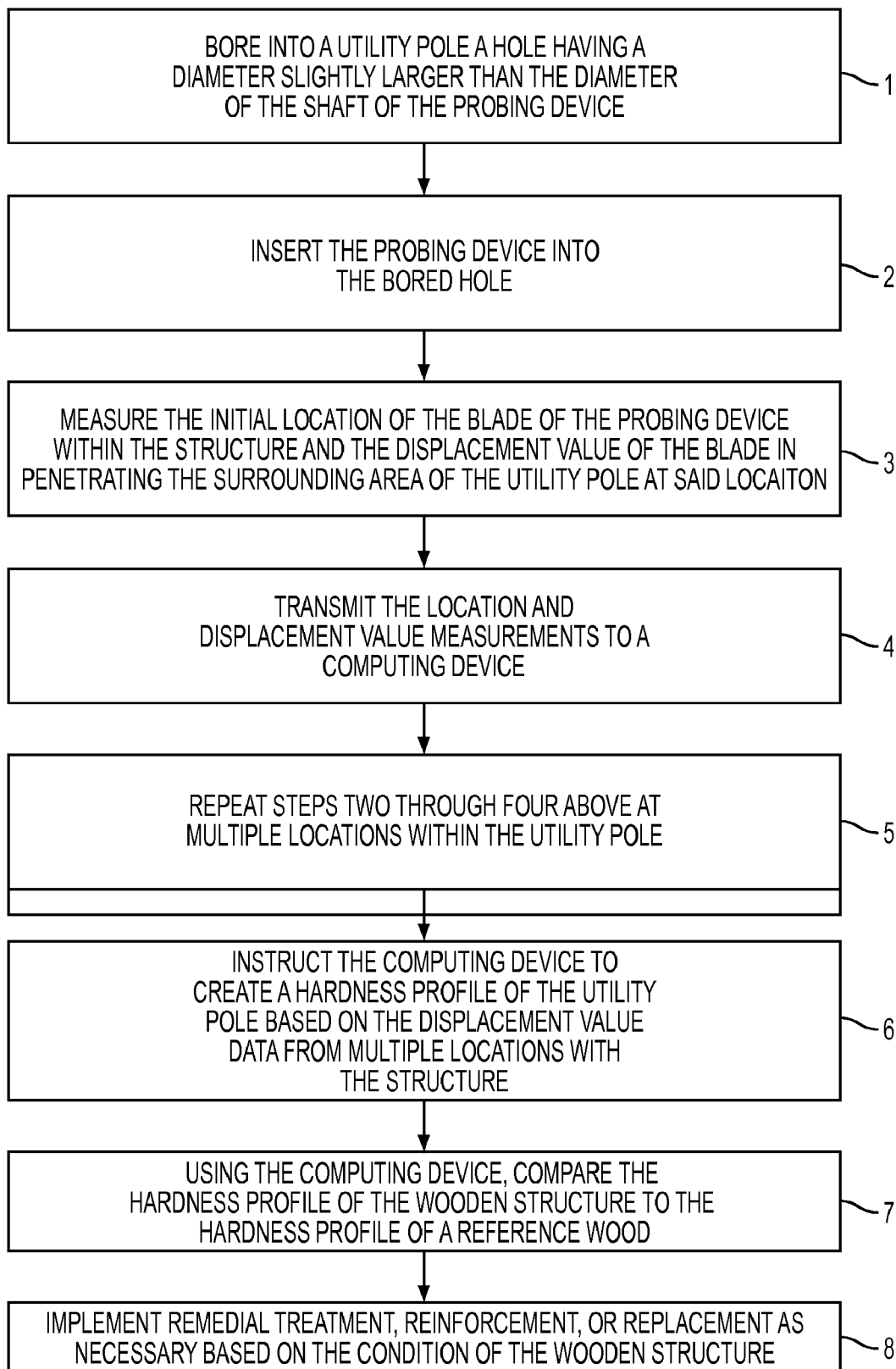

In one embodiment of the present invention, a method of measuring the hardness of a wooden structure by operating a probing device 100 comprises the steps of, as shown in FIG. 15, boring a hole into a wooden structure 112, inserting the probing device 100 into the bored hole, measuring the location of the blade 108 of the probing device 100 within the structure and the displacement value of the blade 108 at the location, and transmitting the location and displacement value data to a computing device 116. In certain embodiments, the location and displacement value measurements and transmissions are repeated at multiple locations within the wooden structure 112, and the data may be compiled and normalized by the computing device 116 to create a hardness profile of the wooden structure 112. In certain aspects, the hardness profile of the wooden structure produced by the method may be compared to a hardness profile of normal wood to determine the condition of the wooden structure. In certain embodiments, a strength calculation can be performed based on the hardness profile of the wooden structure 112. The hardness profile may be used to calculate the section modulus of the structure cross section and the corresponding remaining bending moment capacity, i.e. bending strength. Section modulus is a geometric property for a given cross-section used in the design of beams or flexural members. In certain embodiments, the wooden structure is subsequently subjected to remedial treatment, reinforcement, or replacement based on the condition of the wooden structure. In preferred embodiments, the wooden structure 112 comprises a utility pole.

In certain embodiments, the blade 108 is coupled to a resistance mechanism 110 and a mechanical sensor 114, which are attached to the shaft 106 of a probing device 100, along with a distance sensor 104. The probing device 100 is carefully inserted into the inspection hole, and while the distance sensor 104 measures the location of the blade 108 within the wooden structure 112, the mechanical sensor 114 measures the force on the blade, the displacement value of the blade in the surrounding wood, or another mechanical measurement correlating to the hardness of the surrounding wood.

In certain embodiments, the blade 108 is moved further into the inspection hole. As the blade 108 proceeds through the inspection hole, the distance sensor 104 measures the amount of insertion (i.e., depth) into the structure, and the mechanical sensor 114 measures the amount that the blade 108 is able to penetrate the wood, or the force on the blade, at a given depth within the structure. In certain embodiments, each data point is measured and correlated to the hardness of the wood at the recorded location, using, for example, a computing device 116 coupled to the distance sensor 104 and the mechanical sensor 114. The computing device 116 may be attached to the probing device 100, including for example a visual display to show results of an inspection, or be remote from the probing device 100.

In certain aspects, a computing device 116 capable of receiving and recording data from the distance sensor 104 and the mechanical sensor 114, and is coupled to the probing device 100. The computing device 116 can automatically record the location of the blade within the structure, indicated by the distance sensor 104, and the amount the blade 108 penetrates the wood at that location, the displacement value of the blade 108, or a similar mechanical measure correlating to hardness.

In certain embodiments, an operator 120 carefully inserts the probing device completely through the wooden structure 112, as the computing device 116 records the data described above. The computing device 116 can then normalize the data to create a hardness profile of one or more portions of the wooden structure 112.

In certain embodiments, an operator 120 repeats the steps of inserting the probing device 100 into a second inspection hole, and the computing device 116 again records the measurements. The computing device 116 can then normalize and integrate the data to create a hardness profile of the wooden structure throughout various locations within the structure, including portions of the structure underground. Exemplary wooden structures that may be profiled using the instant invention are wooden poles, wooden timbers, and any other wooden elements susceptible to decay.

In certain embodiments, a probing device 100 may comprise more than one blade (for example blade 108 and second blade 118), more than one resistance mechanism 110, and/or more than one mechanical sensor 114. In this way, an operator 120 can take and record multiple simultaneous measurements during a single insertion of the probing device into a wooden structure 112.

In certain aspects, an operator 120 can insert a probing device 100 into an inspection hole 160, and carefully remove the probing device 100 back through the inspection hole 160 at a rotated angle from the initial entry, such that the probing device 100 measures the hardness of another portion of wood within the structure along the inspection hole 160. As a non-limiting example, an operator 120 may insert the probing device 100 such that the blade 108 rides along the top of the inspection hole 160, and after penetrating through the inspection hole 160, the operator 120 may rotate the probing device 100 about 180 degrees, such that careful removal of the probing device 100 back through the wooden structure 112 results in the blade 108 riding along the bottom of the inspection hole 160.

In one embodiment of the present invention, a system for evaluating the hardness of a wooden structure 112 comprises a probing device 100 coupled to a computing device 116, as shown in FIGS. 13A-13B. Examples of computing devices 116 that may be used in the present invention include PC laptops or desktops, tablets, smartphones, and touch-screen devices. In certain aspects, the probing device 100 can measure the displacement value of a blade 108 within one or more locations within a wooden structure 112, and can transmit the displacement values and corresponding locations to the computing device 116. The connection and transmission between the probing device 100 and the computing device 116 may be wireless, as shown in FIG. 13B. The computing device 116 may alternatively be attached to the probing device 100, so that an operator can view results at the same time as an inspection. The computing device 116 can then correlate the displacement values to hardness of wood to create a hardness profile of the wooden structure 112. In certain embodiments, the probing device measures a force applied by the wood on the blade 108, or another mechanical measure that can be correlated to hardness.

In certain embodiments, the computing device 116 is capable of converting the mechanical measure(s) provided by the probing device 100 to the mass per unit volume hardness of wood, or any other value correlating to the mass per unit volume hardness of wood. For instance, a displacement value of the blade 108, or a resistance to penetration, can be converted to hardness of wood by the computing device 116. In certain embodiments, the computing device 116 may then plot the hardness value against the location within the wooden structure.

Figure 14:
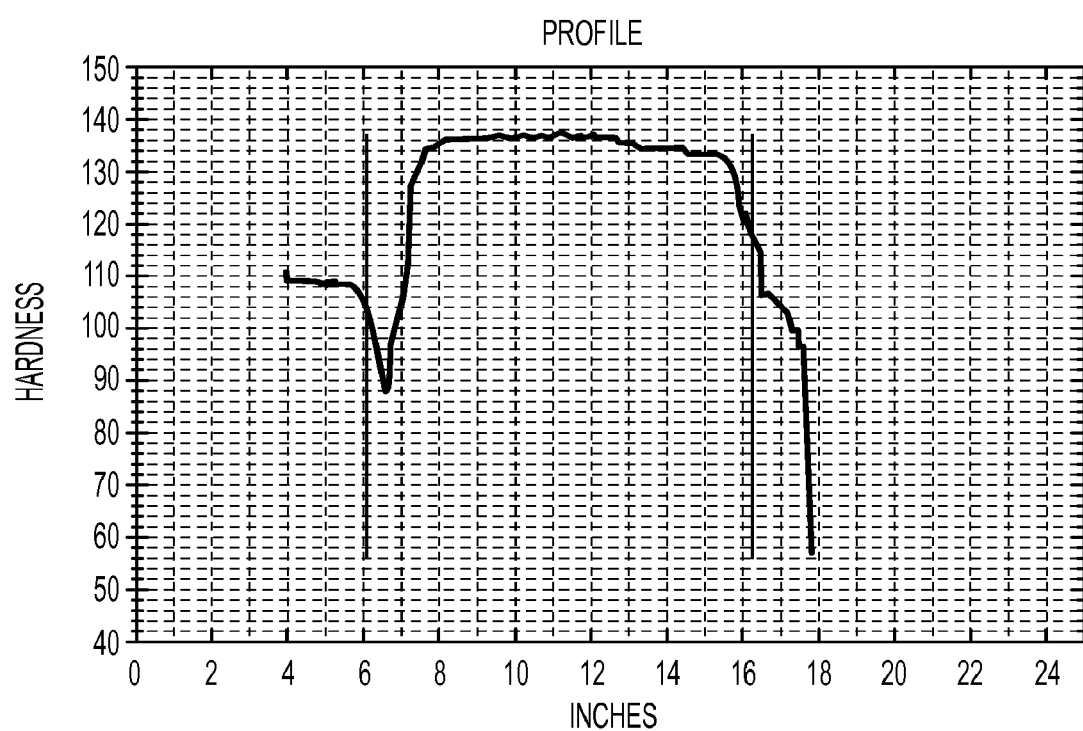

In evaluating the hardness of a wooden structure 112, the computing device 116 is also capable of producing a hardness profile, for example as illustrated in FIG. 14. In certain embodiments, the hardness profile demonstrates the hardness of wood across an inspection hole of a utility pole. The exemplary graph in FIG. 14 plots a measure of hardness, in this example a comparison between the resistance to penetration of the utility pole compared to a reference wood, as a function of depth or location along an inspection hole within the utility pole. The vertical line at about the 16-inch value on the x-axis denotes the location where the blade 108 was introduced into the utility pole, and the vertical line at about the 6-inch value on the x-axis denotes the location where the blade 108 exited the opposite side of the utility pole. The results in FIG. 14 demonstrate a decreased hardness at the location where the probing device exited the wooden structure, which might indicate decay or decomposition in that portion of the wooden structure 112. In certain embodiments, the computing device 116 is attached to the probing device. In other embodiments, the computing device 116 is remote from the probing device.

As a non-limiting example, the computing device 116 may convert incoming data from the probing device 100 into values corresponding to wood hardness, using for example, programs used by those of skill in the art. Thus, the computing device 116, when coupled to the probing device 100, can provide real-time information about the hardness profile of the wooden structure 112 being inspected. An operator 120 may introduce the device 100 into multiple inspection holes to create a hardness profile of a cross-section within the wooden structure 112. In certain aspects, the computing device 116 can also automatically compare the hardness profile of a wooden structure 112 to normal wood, to determine if decay, decomposition, or other irregularities may be present in the structure. In this way, the condition or strength of the wooden structure 112 at one or more cross-sections of the pole can be automatically and accurately analyzed to determine if remedial measures are needed.

In certain embodiments of the methods and systems of the present invention, the wooden structure 112 is subjected to remedial treatments, reinforcement, or replacement based on the condition of one or more areas of the structure. Examples of remedial treatments include preservative pastes (e.g., MP500-EXT®) and bandages (e.g., PoleWrap™), fumigants (e.g., MITC-FUME®, Super-Fume, and Wood-fume®), solid rods (e.g., Bor8 Rods and copper-borate rods), and liquid treatments (e.g., Hollow Heart® CB). Preservative pastes and bandages may be applied, for instance, to address external decay in the areas of a wooden structure at or below ground-line. Fumigants may be applied, for instance, if the condition of the wooden structure indicates areas of internal early or incipient decay. Fumigants can produce vapors that diffuse and travel vertically and horizontally from applications, eliminating wood destroying fungi. Liquid treatments may be applied, for instance, if the condition of the wooden structure indicates areas of internal advanced decay, voids, or cavities. Solid rods may be installed, for example, in pre-drilled holes, such as bolt holes, pole tops, and cross arms, and generally comprise one or more water-soluble wood preservatives. In certain embodiments, based on the condition of one or more areas of a wooden structure, reinforcement of a pole can be implemented by splinting or stubbing a pole using steel channel, reinforcing fiberglass, and epoxy, or by stubbing a pole using a steel channel or fiberglass reinforcing system.

Inspection and Maintenance of Wooden Structures

Hardness profiles determined by the devices, systems, and methods can be used, for example, to determine the capacity remaining in a wooden structure or determine whether a wooden structure is suitable for a particular load, identify structures for remedial treatment or reinforcement, regularly inspect and maintain in-place wooden structures, plan future inspection and maintenance actions of in-place wooden structures, identify a serviceable in-place wooden structure, identify a reinforceable reject in-place wooden structure, and/or identify a replacement candidate in-place wooden structure.

Regular inspection and maintenance of in-place wooden structures, such as wooden poles, is essential to extending the useful life of these structures by ensuring that their wood retains its strength. A comprehensive maintenance program for wooden utility poles, for example, encompasses the monitoring of new attachments and loadings for poles to be certain that the poles are sufficient to carry the new loadings, cyclical in-place inspection and restoration and replacement programs based on new loadings and the results of wood pole inspection, and emergency services. In-place wood pole inspection, as used herein, refers to a nondestructive or minimally-invasive inspection or nondestructive evaluation to determine strength loss in service of a highly variable material, wood, which has been processed, prior to installation, by treatment with wood preservatives to resist attack by wood-destroying organisms such as fungal decay and insects.

While the wood of wooden poles and other wooden structures are initially treated with preservatives that protect against both fungi and insects, loss of these preservatives over time from the wood may leave the structures susceptible to decay from the gradual deterioration caused by fungi and other low forms of plant life (e.g., algae) as well as from infestation by insects including termites, ants, and wood borers. Depending on their geographical location, wooden poles in the United States are classified as being located in one of five "Decay Severity Zones" by the U.S. Department of Agriculture's Rural Utilities Service. Zone 1, where the humidity and temperature is the least conducive to fungal growth and insect infestation, encompasses much of the mountainous West of the United States, whereas Zone 5, the most severe area of decay, is made up of the hot and humid coasts of the southeastern states.

A planned in-place inspection program for wooden poles serves several functions: identifying those poles which present a danger or risk of failure so that those poles can be removed and replaced, identifying poles which are in early stages of damage or decay so that remedial treatments or reinforcement can be applied to those still-serviceable poles to extend their serviceable life, and collecting data and information for planning future inspection and maintenance actions for a system of wood poles. Proper inspection and treatment of wooden poles, depending upon the decay hazards in the area, can extend the serviceable life of those poles by many years.

Spot checking is the initial step in developing a planned pole inspection and maintenance program. Spot checking is a method of sampling representative groups of poles on a system to determine the extent of pole decay and to establish priority candidates for the pole maintenance measures of the program. A general recommendation is to inspect a 1,000-pole sample, made up of continuous pole line groupings of 50 to 100 poles in several areas of the system. The sample should be representative of the poles in place. For instance, all the poles on a line circuit or a map section should be inspected as a unit and not just the poles of a certain age group. Field data should be collected on the sample as to age, supplier, extent of decay, etc.

The data should be analyzed to determine the areas having the most severe decay conditions and to establish priorities for a pole-by-pole inspection of the entire system. It may be desirable to take additional samples on other portions or areas of the system to determine if the severity of decay is significantly different to warrant the establishment of an accelerated pole inspection and maintenance program for that portion of the system. The results of the spot check will aid in scheduling a continuous pole inspection and maintenance program at a rate commensurate with the incidence of decay.

The Rural Utilities Service suggests varying timing for a cyclical pole inspection schedule depending on the geographical Decay Zone in which the wooden poles are located, as the vulnerability of poles to decay is generally proportionate to the decay zone in which they are installed. Poles located in the low-decay Zone 1, for example, should be initially inspected within 12-15 years after installation, with subsequent re-inspection approximately 12 years, and with approximately 1 out of every 12 poles in the system being inspected as representatives of the entire system. In contrast, poles located in the high-decay Zones 4 and 5 should be initially examined within 8-10 years after installation, with subsequent re-inspection every 8 years, and with approximately 1 out of every 8 poles in the system being inspected as representatives of the entire system.

If a spot check indicates that decay is advanced in 1 percent of the pole sample, the inspection and maintenance program should be accelerated so that a higher percentage of poles are inspected and treated sooner than the suggested timelines discussed above. Conversely, if the decay rate is low for a particular decay zone or area in the system, the pole-by-pole inspection can be adjusted accordingly.

After an inspection of wooden poles has been completed, the inspection results are used to update pole plant records, evaluate pole conditions, plan future inspection and maintenance actions, and provide information for system map revisions. The inspection process will result in identifying the condition of each individual pole. The National Electric Safety Code (NESC) requires that if the strength of a structure deteriorates to the level of the overload capacity factors required at replacement, the structure must be replaced or rehabilitated. The inspection results should indicate if a pole is "serviceable" or a "reject."

The NESC designates that a pole is considered "serviceable" when a large portion of completely sound wood exists, or only early stages of decay are present that have not reduced the pole strength below NESC requirements. A pole that does not meet these conditions should be classified as a "reject." Examples of "reject" poles are those that have suffered decay, insect, mechanical, or woodpecker damage that has reduced the pole strength at the ground-line below NESC requirements, or those with hazardous above-ground conditions such as a split top.

Rejected poles may be classified further depending on the severity of their deterioration and whether they are reinforceable. A "reinforceable reject" is a rejected pole which is suitable for restoration of its ground-line bending capacity with an industry-accepted method of reinforcement. A "replacement" candidate is a rejected pole which is not suitable for necessary rehabilitation, and a "priority reject" is a rejected pole that has such severe decay/damage that it should be removed from service as quickly as possible.

Remedial treatments for serviceable wooden poles can interrupt the degradation of a structure by the addition of chemicals, such as pesticides, insecticides, and fungicides, which combat decay and extend the useful life of the structure. Remedial treatments include the application of external preservatives (e.g., pastes or bandages) used for ground-line treatment as well as internal treatments such as liquid internal preservatives, fumigants, and solids. Woodpecker damage can be repaired by plugging woodpecker holes with various materials and covering the plugged hole with a wire mesh to discourage further woodpecker attack. Reinforcement of a pole can be implemented by splinting or stubbing a pole using steel channel, reinforcing fiberglass, and epoxy.

All reference publications or patents cited herein are hereby incorporated by reference in their entirety.

EXAMPLES

The following Examples are only illustrative. It will be readily seen by one of ordinary skill in the art that the present invention fulfills all of the objectives set forth above. After reading the foregoing specification, one of ordinary skill will be able to effect various changes, substitutions of equivalents, and various other aspects of the invention as broadly disclosed therein. It is therefore intended that the protection granted herein be limited only by the definitions contained in the appended claims and equivalents thereof.

Example 1: Probing Device for the Measurement of Hardness in a Wooden Structure An exemplary probing device 100 of the present invention is depicted in FIGS. 1-6. The probing device 100 comprises a shaft 106, a horizontal handle 103, a distance sensor 104, a blade 108, and a mechanical sensor 114, as shown in FIG. 1. The shaft 106 comprises a probing tip 122 at the end of the shaft closest to the blade 108. The probing tip 122 surrounds the blade 108 such that the blade can retract into the probing tip 122 of the shaft 106. The mechanical sensor 114 is housed within the probing tip 122. A resistance mechanism is also housed within the shaft 106.

In this example, the probing tip 122 has a diameter slightly larger than the base of the shaft 106, as shown in FIG. 2. The end of the shaft 106 furthest from the blade is attached to an electronics unit 105, a horizontal handle 103, and a distance sensor 104, as shown in FIG. 3. The electronics unit 105 comprises a housing with electrical components that receive and store data transmitted by the distance sensor 104 and the mechanical sensor 114. The mechanical sensor 114 used in this exemplary embodiment is a strain gauge. The distance sensor 104 used in this example is a short-range sonar. The horizontal handle 103 is attached parallel to the shaft 106 to facilitate ease of use when inspecting a bored hole in a wooden structure.

The shaft 106 of this exemplary embodiment is removable from the horizontal handle 103, electronics unit 105, and distance sensor 104, as shown in FIG. 4. The shaft 106 is attached and removed from these elements using a socket, as shown in FIG. 5. The three conductive prongs shown in FIG. 5 provide electrical connections between the electronics unit 105 and the mechanical sensor 114 located in the shaft 106.

In this exemplary embodiment, the probing tip 122 is removable from the other portion of the shaft, such that the blade 108 can be easily exposed and inspected, as shown in FIG. 6. This configuration facilitates repairs and replacements of the blade 108.

Example 2: Method of Profiling the Hardness of a Wooden Structure

In an exemplary method of the present invention, a probing device 100 is used to measure the hardness of a cross-section of a utility pole. The condition of the wood surrounding a first inspection hole is assessed by boring a hole along a first diameter of a utility pole. The exemplary probing device 100 depicted in FIG. 1 is then introduced into the first inspection hole and carefully inserted through the hole until the blade 108 of the device exits the first inspection hole at the opposite side of the utility pole. As the probing device 100 proceeds through the first inspection hole, the distance sensor 104 continuously measures the location of the blade 108 within the utility pole, and the mechanical sensor 114 continuously measures the strain on the blade 108 caused by contact with the surrounding wood. The location data and the strain data are transmitted to a computing device 116, as shown in FIGS. 13A-13B.

A second inspection hole is bored along a second diameter of a utility pole, where the second diameter is at about a 90 degree angle to the first diameter. To ensure that the inspection holes are bored perpendicular to the utility pole, a V-bracket is mounted to the utility pole using a pilot tube for the bit. The V-bracket serves as a guide for the drill bit to ensure the holes drilled are directed toward the center of the pole at a specific angle to the horizontal plane. The probing device 100 is introduced into, and inserted through the second inspection hole in the same manner as the first inspection hole, and the resulting location data and strain data are transmitted to the computing device 116.

The data is normalized by the computing device 116 to create a hardness profile of the wood along each inspection hole. The hardness profile of the cross-section of the utility pole can then be analyzed, and/or compared to normal wood, to determine the condition of one or more areas of the utility pole and whether any remedial steps are needed. For example, one or more preservatives are applied to areas of external decay; and/or one or more fumigants are applied to areas of early internal decay; and/or one or more liquid treatments are applied to voids and areas of advanced decay. One or more solid rods may also be installed in the bored holes after inspection.

Example 3: Probing Device for the Measurement of Hardness in a Wooden Structure An exemplary probing device of the present invention is depicted in FIGS. 22 and 16-19. The probing device comprises a shaft 106, a raised handle 101, a distance sensor 104, a blade 108, and a dial 107, as shown in FIG. 22. The dial 107 allows a user to adjust the angle of the shaft to inspect an angled bored hole 160 in a wooden structure 112, for example, to inspect an area below the ground-line 170. The shaft 106 comprises a tube 106a, which is secured to the substantial remainder of the shaft by a pin 119, and the triangular metal blade 108 protrudes from an opening at one end of the tube 106a, as shown in FIG. 16. The shaft 106 further comprises a conical probing tip 122 secured by a pin 119 to the end of the tube 106a closest to the blade 106, such that the probing tip 122 is adjacent to the blade 108 and leads the blade 108 into a hole in the wooden structure.

The blade 108 is secured to a pivot arm 109, which is secured to the shaft by a pin 119 that slides through a fitted hole on the end of the pivot arm opposite the blade, as shown in FIG. 17. The blade 108 and the pivot arm 109 sit atop a spring, which is the resistance mechanism 110 in this embodiment. A mechanical sensor 114 (not depicted), an Omega Engineering KFH-3-350-C1-11L3M3R strain gauge, is housed within the shaft 106, connected to the spring, and run through an HX711 24-Bit Analog-to-Digital Converter (from Avia Semiconductor) to convert an analog signal to a digital signal.

The distance sensor 104 is an SP1 50 string potentiometer (from Celesco), using a retractable cable, that outputs a range of voltage as the blade 108 moves forwards through an inspection hole. The string potentiometer runs through an ADS1115 Analog-to-Digital Converter (from Texas Instruments), which converts the voltage to a distance or depth of the blade 108. The probing device also comprises an inclinometer (not depicted), an MMA7455 Digital Acceleration Title Angle Sensor Module (Freescale Semiconductor), that records the angle of the bored hole 160 to the ground-line 170. The angle measured by the inclinometer, in conjunction with the distance or depth recorded by the string potentiometer, provides a location of the blade 108 within the wooden structure 112. Meanwhile, the strain gauge provides the hardness of the area of the wooden structure 112 contacting the blade 108 at said location.

What is claimed is:
1. A device for measuring hardness of wooden structures, the device comprising:
   a shaft comprising an at least partially hollow interior and a hole;

a blade coupled to said shaft, wherein said blade is configured to move inward and outward of said hole;

a resistance mechanism coupled to said blade, said resistance mechanism biasing said blade out of said hole of said shaft toward a protruded position; and a mechanical sensor coupled to said blade, wherein responsive to contacting a wooden structure of sufficient hardness, said blade is configured to displace inwardly into said shaft from said protruded position and said mechanical sensor is configured to measure displacement of said blade.

2. The device of claim 1, wherein said blade is rotatably coupled to said shaft.

3. The device of claim 1, wherein said shaft comprises a probing tip configured to guide, align, or center said shaft within a hole created in said wooden structure.

4. The device of claim 1, wherein said resistance mechanism comprises a spring.

5. The device of claim 1, wherein said shaft has a first end and a second end and said blade is coupled to said shaft in proximity to said second end.

6. The device of claim 1, wherein said shaft further comprises a probing tip that surrounds said blade.

7. A method for measuring hardness of wooden structures, the method comprising the steps of:
(a) inserting a blade into a wooden structure, wherein said blade is coupled to a resistance mechanism such that said resistance mechanism biases said blade toward a protruded position and said blade is configured to displace from said protruded position responsive to contacting a wooden structure of sufficient hardness;
(b) determining a location of said blade in said wooden structure; and
(c) measuring an amount of displacement of said blade with respect to said protruded position at said location using a mechanical sensor.

8. The method of claim 7 further comprising the steps of:
(d) repeating steps (b) through (c) at a second location.

9. The method of claim 8, wherein a hardness of said wooden structure at one or more locations within said wooden structure is correlated with a condition of wood at a location within said wooden structure.

10. The method of claim 8, further comprising the steps of:
creating a hardness profile of said wooden structure based on a plurality of amounts of displacement of said blade at a plurality of locations within said wooden structure; and
comparing said hardness profile of said wooden structure to a hardness profile of a reference wood.

11. The method of claim 10, wherein said measuring step and said comparing step are automated.

12. The method of claim 7, wherein said amount of displacement of said blade is correlated with a hardness of said wooden structure at a location within said wooden structure.

13. The method of claim 7, wherein said method comprises measuring a hardness of an outer surface of said wooden structure.

14. The method of claim 13, wherein said outer surface is below ground level.

15. A system for evaluating hardness of wooden structures, the system comprising:
a device for measuring hardness of wooden structures, the device comprising:
a tube;
a blade coupled to said tube, wherein said blade is configured to move inward and outward of a hole of said blade;
a resistance mechanism coupled to said blade, said resistance mechanism biasing said blade out of said hole of said tube toward a protruded position; and
a mechanical sensor coupled to said blade,
wherein responsive to contacting a wooden structure of sufficient hardness, said blade is configured to displace inwardly into said tube from said protruded position and said mechanical sensor is configured to measure an amount of displacement of said blade; and
a computing device configured to receive and process data from said device.

16. The system of claim 15, further comprising a device configured to create a hole in said wooden structure.

17. The system of claim 15, wherein said computing device is configured to receive, from said device, data indicating said amount of displacement of said blade at said location in said wooden structure.

18. The system of claim 17, wherein said computing device is configured to determine a hardness of said wooden structure from said amount of displacement of said blade at said location.

19. The system of claim 15, wherein said computing device is programmed to create a hardness profile of said wooden structure.

20. The system of claim 19, wherein said computing device is programmed to compare the hardness profile of said wooden structure to a hardness profile of a reference wood to determine a condition of said wooden structure.

* * * * *